(12) United States Patent
Zhou et al.

(10) Patent No.: US 6,806,050 B2
(45) Date of Patent: Oct. 19, 2004

(54) INDIVIDUALLY ADDRESSABLE MICRO-ELECTROMAGNETIC UNIT ARRAY CHIPS

(75) Inventors: Yuxiang Zhou, Beijing (CN); Litian Liu, Beijing (CN); Ken Chen, Beijing (CN); Depu Chen, Beijing (CN); Jia Wang, Beijing (CN); Zewen Liu, Beijing (CN); Zhimin Tan, Beijing (CN); Junquan Xu, Putian (CN); Xiaoshan Zhu, Dan Yang (TW); Xuezhong He, Luuyang (CN); Wenzhang Xie, Harbin (CN); Zhiming Li, Xiameng (CN); Xiumel Liu, Beijing (CN)

(73) Assignee: AVIVA Biosciences, San Diego, CA (US)

( * ) Notice: Subject to any disclaimer, the term of this patent is extended or adjusted under 35 U.S.C. 154(b) by 315 days.

(21) Appl. No.: 09/955,343

(22) Filed: Sep. 18, 2001

(65) Prior Publication Data

US 2002/0022276 A1 Feb. 21, 2002

Related U.S. Application Data

(62) Division of application No. 09/399,299, filed on Sep. 17, 1999, now Pat. No. 6,355,491.

(30) Foreign Application Priority Data

| Mar. 15, 1999 | (CN) | 99104113 |
| Sep. 16, 1999 | (CN) | 99120320 |

(51) Int. Cl.[7] .......................................... G01N 33/543
(52) U.S. Cl. .................. 435/6; 435/4; 435/7.1; 435/287.1; 435/287.2; 422/82.01; 436/149; 436/150; 436/151; 436/518; 436/526; 436/806
(58) Field of Search ................ 435/4, 6, 7.1, 287.1, 435/287.2; 422/82.01; 436/518, 526, 806, 149, 150, 151

(56) References Cited

U.S. PATENT DOCUMENTS 4,160,645 A 7/1979 Ullman (List continued on next page.)

FOREIGN PATENT DOCUMENTS

| DE | 43 36 417 | 4/1994 |
| WO | WO 94/16101 | 7/1994 |
| WO | WO 98/14641 | 4/1998 |
| WO | WO 00/33062 | 6/2000 |
| WO | WO 00/54882 | 9/2000 |
| WO | WO 02/31505 | 4/2002 |

OTHER PUBLICATIONS

Ahn and Allen, IEEE Transactions on Magnets, 30:73–79 (1994).
Ahn and Allen, Electrochemical Society Proceedings, 95–18:411–425.

(List continued on next page.)

*Primary Examiner*—Christopher L. Chin
(74) *Attorney, Agent, or Firm*—David R. Preston & Associates APC; David Preston

(57) ABSTRACT

This invention provides electromagnetic chips and electromagnetic biochips having arrays of individually addressable micro-electromagnetic units, as well as methods of utilizing these chips for directed manipulation of micro-particles and micro-structures such as biomolecules and chemical reagents. An electromagnetic biochip comprises an individually addressable micro-electromagnetic unit chip with ligand molecules immobilized on its surface. By controlling the electromagnetic field at each unit of the array and combining this control with magnetic modification of biomolecules, these chips can be used for directed manipulation, synthesis and release of biomolecules in order to increase sensitivity of biochemical or chemical analysis and reduce assay time. Other advantages with these chips include minimized damages to biological molecules and increased reproducibility of assay results.

25 Claims, 12 Drawing Sheets

U.S. PATENT DOCUMENTS

| | | |
|---|---|---|
| 4,275,149 A | 6/1981 | Litman et al. |
| 4,318,980 A | 3/1982 | Boguslaski et al. |
| 4,777,019 A | 10/1988 | Dandekar |
| 4,894,443 A | 1/1990 | Greenfield et al. |
| 5,122,227 A | 6/1992 | Ott |
| 5,202,231 A | 4/1993 | Drmanac et al. |
| 5,225,969 A | 7/1993 | Takaya et al. |
| 5,238,810 A | 8/1993 | Fujiwara et al. |
| 5,252,493 A | 10/1993 | Fujiwara et al. |
| 5,252,743 A | 10/1993 | Barrett et al. |
| 5,439,586 A | 8/1995 | Richards et al. |
| 5,445,934 A | 8/1995 | Fodor et al. |
| 5,605,662 A | 2/1997 | Heller et al. |
| 5,612,474 A | 3/1997 | Patel |
| 5,624,711 A | 4/1997 | Sundberg et al. |
| 5,632,957 A | 5/1997 | Heller et al. |
| 5,653,939 A | 8/1997 | Hollis et al. |
| 5,655,665 A | 8/1997 | Allen et al. |
| 5,779,976 A | 7/1998 | Leland et al. |
| 5,833,760 A | 11/1998 | Huh et al. |
| 5,849,486 A | 12/1998 | Heller et al. |
| 5,856,174 A | 1/1999 | Lipshutz et al. |
| 5,858,666 A | 1/1999 | Weiss |
| 5,874,554 A | 2/1999 | Gamble et al. |
| 5,883,760 A | 3/1999 | Yamada et al. |
| 6,051,380 A | 4/2000 | Sonsnowski et al. |
| 6,187,164 B1 | 2/2001 | Warren et al. |
| 6,355,491 B1 | 3/2002 | Zhou et al. |

OTHER PUBLICATIONS

Ahn et al., Journal of Microelectrochemical Systems, 5:151–158 (1996).
Baselt et al, Biosensors & Bioelectronics, 13:731–739 (1998).
Batra et al., Molecular Immunology, 30:379–386 (1993).
Blanchard et al., Biosensors & Bioelectronics, 11:687–690 (1996).
Brown and Hartwell, Nature Genetic, 18:91–93 (1998).
Chee et al., Science, 274:610–614 (1996).
Drmanac et al., Nature Biotechnology, 16:54–58 (1998).
Edelstein et al., Biosensors & Bioelectronics, 14:805–813 (2000).
Gascoyne et al. IEEE Transactions on Industry Applications, 33:670–678 (1997).
Huston et al., Proc. Natl. Acad. Sci. USA, 85:5879–5883 (1988).
Ju et al., Proc. Natl. Acad. Sci. USA, 92:4347–4351 (1995).
Ladurner and Fersht, J. Mol. Biol., 273:330–337 (1997).
Liakopoulos et al, TRANSDUCERS '97, pp. 485–488 (1997).
Livache et al, Analytical Biochemistry, 255:188–194 (1998).
Marton et al, Nature Medicine, 4:1293–1301 (1998).
Milner et al., Nature Biotechnology, 15:537–541 (1997).
Miyabayshi et al., Biotech. Appl. Biochem. 11:379–386 (1989).
Newton et al, Biochemistry, 35:545–553 (1996).
Ruan et al., The Plant Journal, 15:821–833 (1998).
Schena et al., Science, 270:467–470 (1995).
Shoemaker et al., Nature Genetics, 14:450–456 (1996).
Sosnowski et al., Proc. Natl. Acad. Sci. USA, 94:1119–1123 (1997).
Sun et al., Cytometry, 33:469–475 (1998).
Whitlow et al., Protein Engineering, 6:989–995 (1993).
Wang, D. et al., Science, 280:1077–1082 (1998).
Wang, X., et al., IEEE Transactions on Industry Applications, 33:660–669 (1997).
Wodicka et al., Nature Biotechnology, 15:1359–1367 (1997).

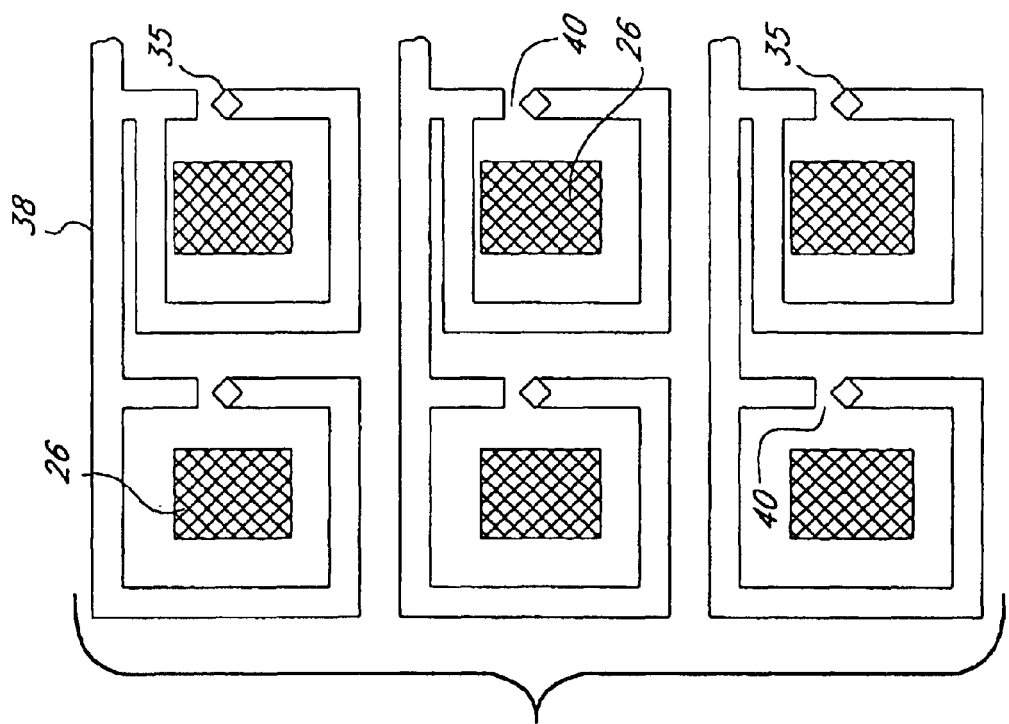
FIG. 8
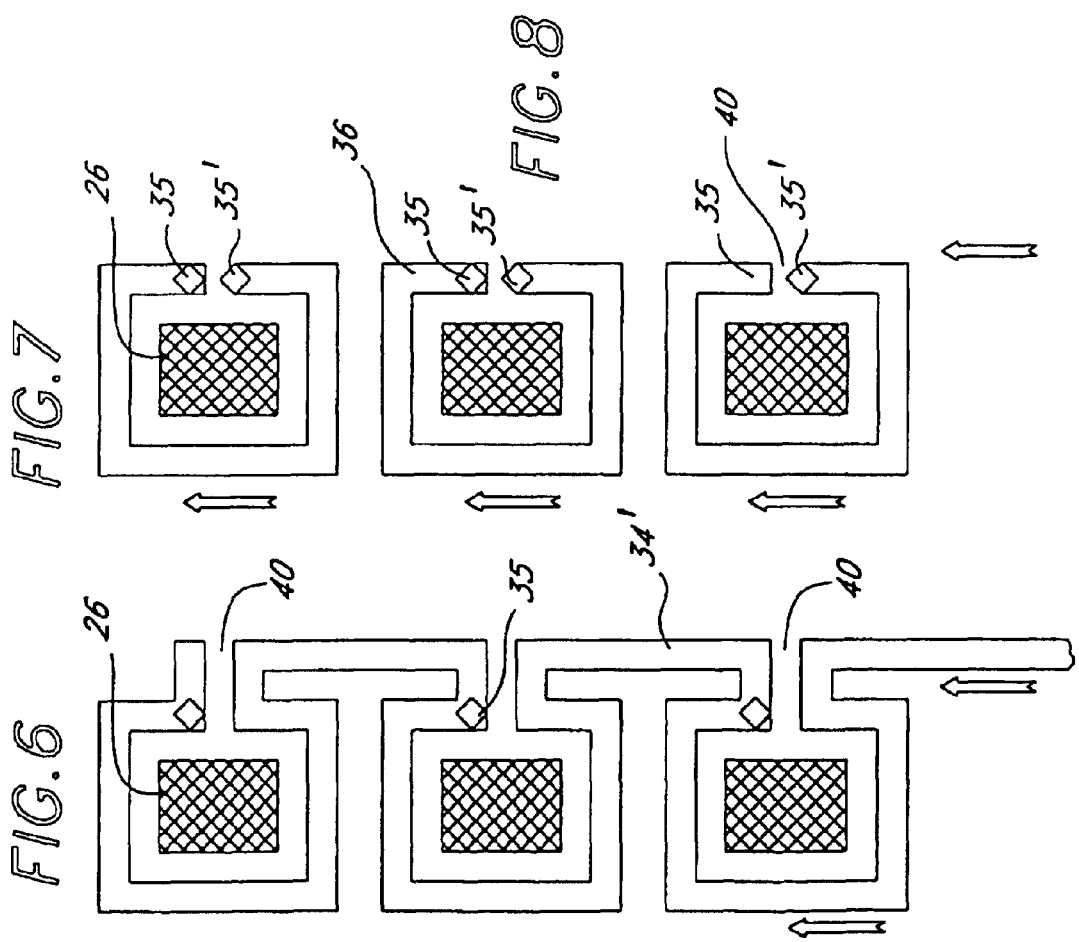
FIG. 7
FIG. 6

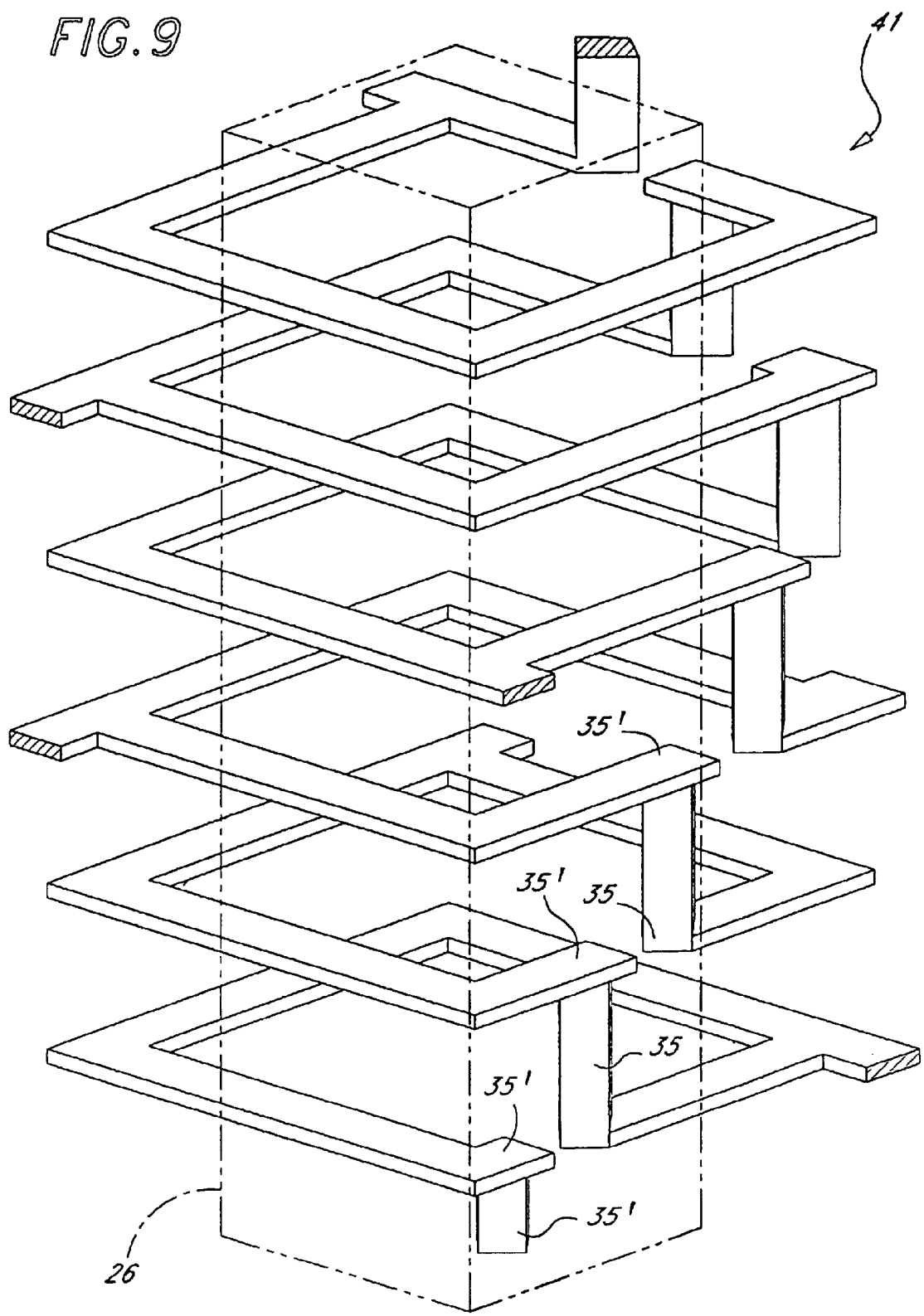

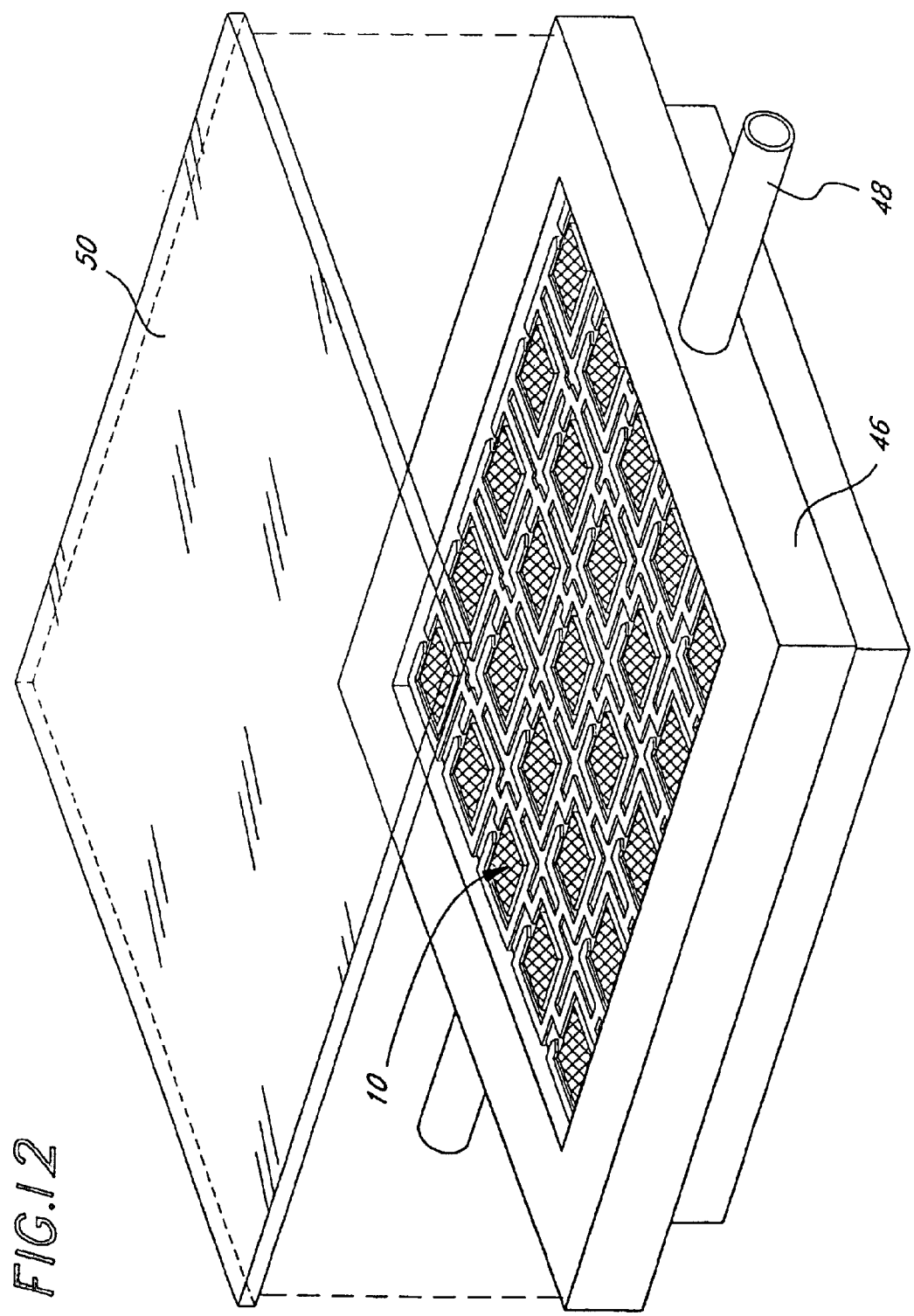

FIG.13
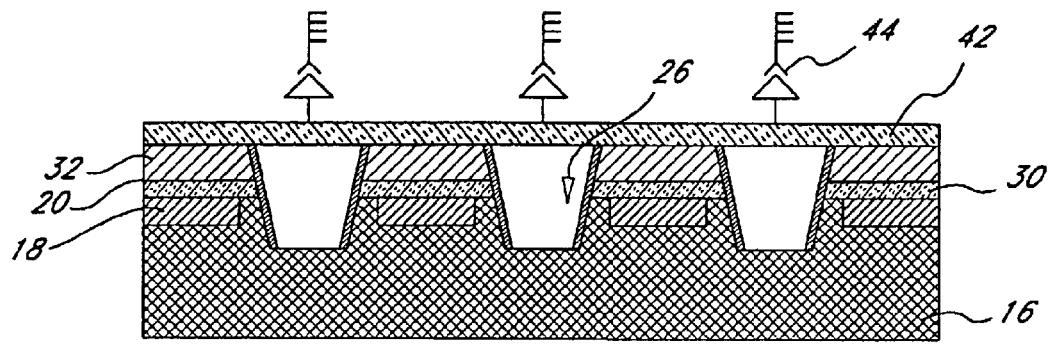
FIG.14
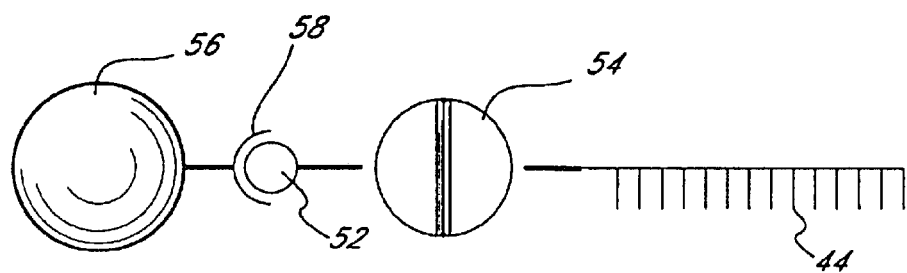
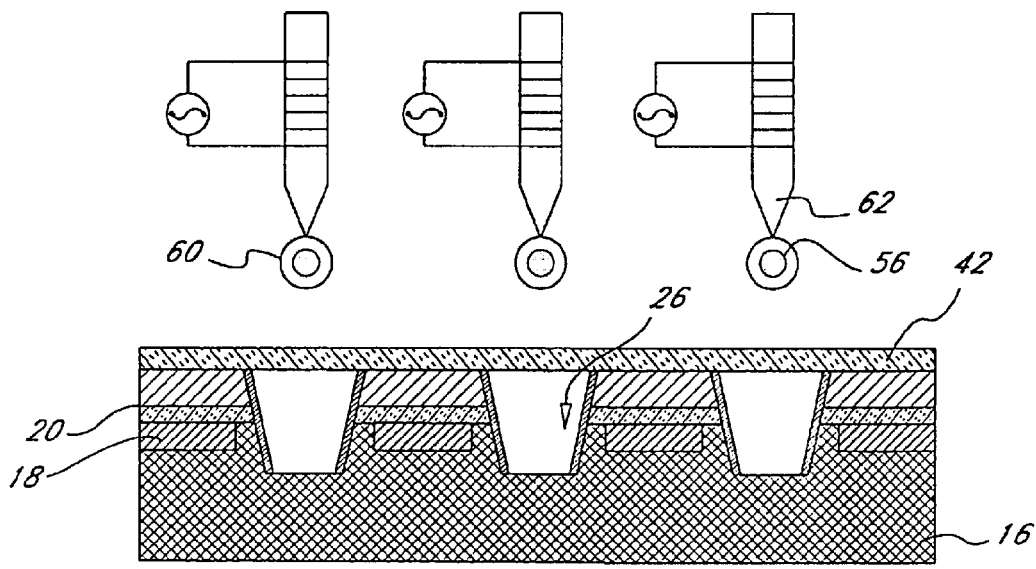
FIG.15

INDIVIDUALLY ADDRESSABLE MICRO-ELECTROMAGNETIC UNIT ARRAY CHIPS

The present application is a Divisional of U.S. patent application Ser. No. 09/399,299, entitled, "Individually Addressable Micro-Electromagnetic Unit Array Chins," filed on Sep. 17, 1999, now U.S. Pat. No. 6,355,491 and claims priority to People's Republic of China Application No. 99104113.5 entitled "Individually Addressable Micro-Electromagnetic Unit Array Chips, Electromagnetic Biochips and Their Applications," filed on Mar. 15, 1999, and People's Republic of China Application No. 99120320.8, filed on Sep. 16, 1999, each of which are incorporated herein by reference.

FIELD OF THE INVENTION

The present application concerns micromachined or microfabricated devices known as "biochips" and more particularly biochips employing magnetic forces and methods of utilizing such biochips for performing chemical, biological and biochemical reactions and assays.

DESCRIPTION OF RELATED ART

As a novel and emerging technology in life science and biomedical research during last several years, biochip technology can be applied to many areas of biology, biotechnology and biomedicine including point-mutation detection, DNA sequencing, gene expression, drug screening and clinical diagnosis. Biochips refer to miniaturized devices having characteristic dimensions in the micrometer to millimeter range that can be used for performing chemical and biochemical reactions. Biochips are produced using microelectronic and microfabrication techniques as used in semiconductor industry or other similar techniques, and can be used to integrate and shrink the currently discrete chemical or biochemical analytical processes and devices into microchip-based apparatus. Recent scientific literature shows a plethora of uses for these devices.

The reader's attention is drawn to the following articles for an appreciation of the breadth of biochip uses. "Rapid determination of single base mismatch mutations in DNA hybrids by direct electric field control" by Sosnowski, R. G. et al. (Proc. Natl. Acad. Sci., USA, 94:1119–1123 (1997)) and "Large-scale identification, mapping and genotyping of single-nucleotide polymorphisms in the human genome" by Wang, D. G. et al. (Science, 280: 1077–1082 (1998)) show current biochip use in detection of point mutations. "Accurate sequencing by hybridization for DNA diagnostics and individual genomics." by Drmanac, S. et al. (Nature Biotechnol. 16: 54–58 (1998)), "Quantitative phenotypic analysis of yeast deletion mutants using a highly parallel molecular bar-coding strategy" by Shoemaker, D. D. et al. (Nature Genet., 14:450–456 (1996)), and "Accessing genetic information with high density DNA arrays." by Chee, M et al., (Science, 274:610–614 (1996)) show biochip technology used for DNA sequencing. The use of biochip technology to monitor gene expression is shown in "Genome-wide expression monitoring in Saccharomyces cerevisiae" by Wodicka, L. et al. (Nature Biotechnol. 15:1359–1367 (1997)), "Genomics and human disease—variations on variation," by Brown, P. O. and Hartwell, L. and "Towards Arabidopsis genome analysis: monitoring expression profiles of 1400 genes using cDNA microarrays." by Ruan, Y. et al. (The Plant Journal 15:821–833 (1998)). The use of biochips in drug screening is illustrated in "Selecting effective antisense reagents on combinatorial oligonucleotide arrays." by Milner, N. et al. (Nature Biotechnol., 15:537–541 (1997)), and "Drug target validation and identification of secondary drug target effects using DNA microarray." by Marton, M. J. et al. (Nature Medicine, 4:1293–1301 (1998)). Examples of clinical diagnostic use of biochips are illustrated in "Cystic fibrosis mutation detection by hybridization to light-generated DNA probe arrays." by Cronin, M. T. et al. (Human Mutation, 7:244–255 (1996)), and "Polypyrrole DNA chip on a silicon device: Example of hepatitis C virus genotyping." by Livache, T. et al. (Anal. Biochem. 255:188–194 (1998)). These references are intended to give a notion of the wide range of biochip uses.

A variety of biochips have biomolecules (e.g., oligonucleotides, cDNA and antibodies) immobilized on their surfaces. There are a number of different approaches to make such chips. For example, the light-directed chemical synthesis process developed by Affymetrix (see, U.S. Pat. Nos. 5,445,934 and 5,856,174) is a method of synthesizing biomolecules on chip surfaces by combining solid-phase photochemical synthesis with photolithographic fabrication techniques. The chemical deposition approach developed by Incyte Pharmaceutical uses pre-synthesized cDNA probes for directed deposition onto chip surfaces (see, e.g., U.S. Pat. No. 5,874,554). The contact-print method developed by Stanford University uses high-speed, high-precision robot-arms to move and control a liquid-dispensing head for directed cDNA deposition and printing onto chip surfaces (see, Schena, M. et al. Science 270:467–70 (1995)). The University of Washington at Seattle has developed a single-nucleotide probe synthesis method using four piezoelectric deposition heads, which are loaded separately with four types of nucleotide molecules to achieve required deposition of nucleotides and simultaneous synthesis on chip surfaces (see, Blanchard, A. P. et al. Biosensors & Bioelectronics 11:687–90 (1996)). Hyseq, Inc. has developed passive membrane devices for sequencing genomes (see, U.S. Pat. No. 5,202,231).

There are two basic types of biochips, i.e., passive and active. Passive biochips refer to those on which chemical or biochemical reactions are dependent on passive diffusion of sample molecules. In active biochips reactants are actively moved or concentrated by externally applied forces so that reactions are dependant not only on simple diffusion but also on the applied forces. The majority of the available biochips, e.g., oligonucleotide-based DNA chips from Affymetrix and cDNA-based biochips from Incyte Pharmaceuticals, belongs to the passive type. There are structural similarities between active and passive biochips. Both types of biochips employ of arrays of different immobilized ligands or ligand molecules. Herein, "ligands or ligand molecules" refers to bio/chemical molecules with which other molecules can react. For instance, a ligand may be a single strand of DNA to which a complementary nucleic acid strand can hybridize. A ligand may be an antibody molecule to which the corresponding antigen (epitope) can bind. A ligand may also include a particle on whose surface are a plurality of molecules to which other molecules may react. By using various markers and indicator molecules (e.g.: fluorescent dye molecules), the reaction between ligands and other molecules can be monitored and quantified. Thus, an array of different ligands immobilized on a biochip enables the reaction and monitoring of multiple analyte molecules.

Many current passive biochip designs do not take full advantage of microfabrication and microelectronic technologies. Passive biochips cannot be readily used to achieve fully integration and miniaturization of the entire bioanalytical system from the front-end sample preparation to final molecular quantification/detection. In addition, passive biochips have other disadvantages including low analytical sensitivity, a long reaction time, and difficulties associated with control of temperature, pressure, and electrical fields at individual sites (called units) on the chip surfaces as well as difficulties in controlling the local concentrations of molecules.

On the other hand, active biochips allow versatile functions of molecular manipulation, interaction, hybridization reaction and separation (such as PCR and capillary electrophoresis) by external forces through means such as microfluidic manipulation and electrical manipulation of molecules. However, many such biochips cannot be readily used in high throughput applications. The electronic biochips developed by Nanogen can manipulate and control sample biomolecules with electrical field generated by microelectrodes, leading to significant improvement in reaction speed and detection sensitivity over passive biochips (see, U.S. Pat. Nos. 5,605,662, 5,632,957, and 5,849,486). However, to effectively move biomolecules in their suspension/solutions with electrical fields, the electrical conductivity of solutions has to be very low. This significantly limits the choice of buffer solutions used for biochemical assays because enzymes and other biomolecules are denatured under conditions of low ionic strength and/or serious non-specific binding occurs to chip surfaces.

The present invention provides a new type of active biochips in which magnetic forces are generated by individually addressable (controllable) units arranged in an array. The magnetic forces are used to control and manipulate magnetically modified molecules and particles and to promote molecular interactions and/or reactions on the surface of the chip. Magnetic forces have been widely employed in biological, biochemical and biomedical applications. For example, magnetic-activated cell sorting is a common technique based on selectively binding magnetic particles that has been modified with antibodies to specific cell types within a mixture. After binding, the cell-magnetic particle complexes from the cell mixture are selectively removed using a magnet. (See, for example, Miltenyi, S. et al. "High gradient magnetic cell-separation with MACS." Cytometry 11:231–236 (1990)). Other examples were given in U.S. Pat. No. 5,439,586 describing a three-dimensional magnetic filter for separating magnetically labeled particles from non-magnetic particles in a flow stream and in U.S. Pat. No. 5,655,665 disclosing a micromachined magnetic particle separator for microfluidic magnetic separations.

SUMMARY OF THE INVENTION

The present invention discloses electromagnetic biochips that comprise individually addressable micro-electromagnetic units arranged in arrays. An array refers to a plurality of micro-electromagnetic units. An electromagnetic biochip may have single or multiple micro-electromagnetic unit arrays. Each unit is capable of inducing magnetic field upon the application of electric current, and is selectively addressable so that the magnetic filed generated by the unit can be turned on or off and/or can be modulated in terms of the field intensity and field direction through alteration of the electric current applied to the unit. Magnetic fields on the chip's surface are then used to manipulate magnetic particles or magnetically-modified/loaded biomolecules. The magnetic particles or molecules are actually guided to predetermined locations on the chip's surface. The chip's surface may be chemically modified to form a functional layer for immobilizing ligand molecules so that affinity interaction or specific chemical reactions may occur between the ligand molecules and the magnetically guided particles or molecules. Magnetic guiding and manipulation of particles or molecules can increase the local concentration of these materials so as to increase the rate of biochemical or chemical reactions and the sensitivity of various assays. Because ionic strength and other buffer characteristics have little or no effect on magnetic fields, biochemically optimized buffer conditions can be selected. Furthermore, no strong electrical fields are present to complicate the assay or reaction by electrochemistry.

Micro-electromagnetic units are fabricated on substrate materials and generate individual magnetic fields when electric currents are applied. One example of the unit is a single loop of electrical conductor wrapped around a ferromagnetic body or core and connected to an electric current source through electronic switches. Such a loop may be a circle, ellipse, spiral, square, triangle or other shapes so long as a flow of electric current can be facilitated around the ferromagnetic body. If the loop is single, it should be complete or substantially complete. The loop may be in the form of a plurality of turns around the ferromagnetic body (either in one plane or stacked as in a coil). The turns may be fabricated within a single layer of the microstructure, or, alternatively, each turn may represent a separate layer of the structure. The electric conductor may be a deposited conductive trace—as in a electroplated, sputtered or deposited metallic structure, or the conductor may be formed within a semiconductor layer through selective doping. A preferred arrangement of an array of a plurality of micro-electromagnetic units has a column and row structure of the form common in microelectronics. That is, the columns and rows are mutually perpendicular although the columns and rows can readily be offset at different angles (e.g., 80 degrees).

The individual micro-electromagnetic units in a single chip may be of a single shape and dimension or there may be a variety of unit shapes and sizes within one chip. Characteristic dimensions of a unit vary from less than one micrometer to as large as one centimeter. The characteristic dimension refers to, for example, a diameter for a circle loop unit or a side length for a square loop unit. It will be apparent to one of ordinary skill in the art that where it is desired to react a large number of ligand molecules a larger unit size can be used. The units may be arranged in a regular, repetitive pattern (e.g., a rectangular grid) or they may be arranged in an "irregular" or "random" pattern.

Individual micro-electromagnetic units may be selectively addressable so that at any instant there may be only a single energized unit generating a local magnetic field or there may be multiple energized units generating more or less complex magnetic fields. Addressing a micro-electromagnetic unit means applying electric current to energize the unit and to generate magnetic field in its vicinity. Electric current amplitudes and directions are selected so that energized units produce fields of sufficient intensity to attract and move magnetic particles or magnetically modified molecules. Units that are not selectively energized may be completely "off" (i.e., zero magnetic field) or such units may produce magnetic fields of insufficient intensity to attract or otherwise move the magnetic particles.

Selective addressing of individual units can be achieved in a number of ways. For example, where each unit contains a single loop of electric conductor one end of the loop can be connected to an electric current source (through electrical switching means) while the other end of the loops is attached to an electric current sink so that a current will flow through the loop. In another example, as explained below, units in a column/row array can be selectively activated by attaching (through switching means) a row to, for example, a current source and a column (through switching means) to a current sink. This will energize the unit at the intersection of the column and row.

The present invention further discloses methods for manipulating magnetic particles on electromagnetic chips. The particles may be suspended in a fluid (either aqueous or non-aqueous liquid or a gas) or even in a vacuum. When a micro-electromagnetic unit is energized, magnetic particles in the vicinity of that unit will experience magnetic forces and are attracted to the surface of the energized unit. That is, where a suspension of magnetic particles covers the entire chip array, energizing a single electromagnetic unit will affect only particles in the immediate vicinity of the energized unit. However, by sequentially energizing units it is possible to move and concentrate all of the magnetic particles suspended over the entire array. Such coordinated movement is referred to as "manipulation" and such manipulation can be controlled by switching units on and off in a predetermined sequence. Manipulation of magnetic particles also refers to the change and control of particle position, velocity and other kinetic properties by modulating electric currents applied to micro-electromagnetic units and accordingly altering magnetic field distribution and forces acting on particles. Depending on the application, all units or some of the units may be energized simultaneously. Alternatively, units may be energized one-at-a-time.

Magnetic particles or materials used with the present invention may be of different sizes ranging from nanometer dimensions to micrometer or even millimeter dimensions. Magnetic particles may be of a variety of materials and be manufactured by a number of different processes as long as the magnetic fields produced by the biochips of the present invention can induce a sufficient magnetic dipole-moment in the particles.

The present invention further discloses methods for manipulating biomolecules/bioparticles, chemical-reagent molecules, drug molecules or any other molecules or particles with an electromagnetic biochip. These biochips can generally be used to manipulate any kind of magnetic particle. For controlling and handling non-magnetic particles and/or biomolecules, these materials are first magnetically modified. For example, the molecules may be covalently attached or physically absorbed to the surface of magnetic particles. The biomolecules may be proteins (e.g., antibodies, antigens and receptors), nucleic acids (e.g., single stranded DNA or RNA) or other molecules such as lipids or carbohydrates. The electromagnetic biochip surface may be modified for immobilizing ligand molecules that are capable of interacting with molecules on the surface of the manipulated magnetic particles. Such interactions are facilitated because the magnetic particles are concentrated at specific locations on which the appropriate ligand molecules are already immobilized.

In solutions, binding or reaction between molecules (e.g., antibody+antigen; specific DNA probe and its complementary single-stranded target DNA) occur as the molecules collide during diffusion. The efficiency and speed of the reactions depend on the local concentration of the reacting molecules and the kinetic energy of their collisions. In many biochip-based systems one type of molecule is immobilized at the chip surface while another type of molecule is present in a solution on the chip surface. Reactions occur when molecules passively diffusing in the solution collide with the immobilized molecules. Only a small percentage of the molecules in the solution actually diffuse and collide in a reasonable amount of time. Thus, the reactions are slow and inefficient, severely limiting the speed, efficiency and the sensitivity of bio/chemical assays performed on these biochips. In the electromagnetic biochips of the present invention the molecules in solution are actively brought into contact with the immobilized molecules on the chip surface by means of magnetic forces. The resulting reactions are "actively" driven by magnetic force leading to improved speed, efficiency and sensitivity.

For a typical magnetic particle of super-paramagnetic material, a magnetic dipole $\bar{\mu}$ is induced in the particle when it interacts with a magnetic field $\overline{B}$.

$$\bar{\mu} = V_p(\chi_p - \chi_m)\frac{\overline{B}}{\mu_m}, \quad (1)$$
$$= V_p(\chi_p - \chi_m)\overline{H}_m$$

where $V_p$ is the particle volume, $\chi_p$ and $\chi_m$ are the volume susceptibility of the particle and its surrounding medium $\mu_m$ is the magnetic permeability of medium, $\overline{B}$ is the magnetic field strength. The magnetic force $\overline{F}_{magnetic}$ acting on the particle is determined by the magnetic dipole moment and the magnetic field gradient:

$$\overline{F}_{magnetic} = -0.5V_p(\chi_p - \chi_m)\vec{H}_m \circ \nabla \vec{B}_m, \quad (2)$$

where the symbols "$\circ$" and "$\nabla$" refer to dot-product and gradient operations, respectively. The particle velocity $v_{particle}$ under the balance between magnetic force and viscous drag is given by:

$$v_{particle} = \frac{\overline{F}_{magnetic}}{6\pi r \eta_m} \quad (3)$$

where r is the particle radius and $\eta_m$ is the viscosity of the surrounding medium. Thus to achieve sufficiently large magnetic manipulation force, the following factors should be considered:

(1) Particle susceptibility should be maximized;
(2) Magnetic field strength should be maximized; and
(3) Magnetic field strength gradient should be maximized.

We will now describe several illustrative embodiments of the present invention. According to one embodiment of the present invention, an individual addressable micro-electromagnetic unit column-row array chip comprises:

a substrate;
an array of cavities on the substrate;
a ferromagnetic core in each cavity;
a first layer of conductive traces on the substrate running between the columns of ferromagnetic cores;
a first insulation layer on the substrate surface that covers the first layer of conductive traces;
a second layer of conductive traces on the surface of the first insulation running between the rows of ferromagnetic cores, perpendicular to the first conductive traces;
a second insulation layer on the chip surface that covers the ferromagnetic core array and the second layer of conductive traces.

In another embodiment of the present invention, an electromagnetic biochip comprises an individually addressable micro-electromagnetic unit array chip that comprises a substrate;
an array of cavities on the substrate;
an magnetic-core in each cavity;
a first layer of conductive traces on the substrate running between every columns of magnetic-cores;

a first insulation layer on the substrate surface that covers the first layer of conductive traces;

a second layer of conductive traces on the surface of the first insulation layer running between each rows of magnetic-cores perpendicular the first layer conductive traces;

a second insulation layer on the chip surface that covers the magnetic-core array and the second layer of conductive traces;

a thin binding layer (i.e., a functional layer) that covers the second insulation layer and is used to immobilize ligand molecules thereon; and ligand molecules that are directed and immobilized onto the thin functional layer using magnetic forces or other methods.

The functional layer is used for immobilizing ligand molecules. Examples of a functional layer include, but are not limited to, a molecular monolayer, a membrane, a gel, and a porous or non-porous material layer. The functional layer may be an additional layer adhered to the biochip surface (in the above example, to the second insulation layer). Alternatively, the functional layer may be formed by direct chemical-modification of the biochip surface molecules. In the example above, the surfaces of the second insulation layer may be chemically modified to contain chemical groups or molecular sites for binding or attaching ligand molecules. Ideally, the functional layer should show minimal or no non-specific bindings to molecules other than ligand molecules and should allow efficient binding or attachment of ligand molecules.

According to one embodiment of the present invention, a method for manipulating biomolecules, chemical reagents, or drug molecules comprises these steps:

providing the above-described individually addressable micro-electromagnetic unit array chips;

forming a thin binding layer (i.e., a functional layer) for immobilizing ligand molecules on the chip's surface;

loading micro-locations on the binding layer with a set of ligand molecules by positioning and immobilizing magnetically-modified ligand molecules at predetermined micro-locations to form molecule-binding regions on the chip surface by selectively controlling electric current in the conductive traces in the micro-electromagnetic unit array chip to produce magnetic fields around desired micro-electromagnetic units;

magnetically modifying or loading target molecules by linking them with magnetic beads;

introducing solutions containing magnetic bead-linked target molecules onto the above-described ligands-containing micro-electromagnetic unit array chip;

producing magnetic fields around desired micro-locations by selectively addressing and energizing particular units within micro-electromagnetic unit array so that magnetically modified target molecules can be directed toward ligand molecules on the desired unit locations so as to accomplish binding reactions; and releasing magnetic beads from target molecules followed by removal of the magnetic beads.

The ligands and target molecules in the above method may be biological molecules, chemical reagents, drug-candidate molecules, or any other molecules or particles. Methods according to the present invention may be used for hybridization and detection for specific sequences of DNA molecules, for antibody/antigen binding interaction in application areas such as drug screening, bio/chemical (i.e., biochemical or chemical) process control, biochemical monitoring and clinical diagnosis.

In the, following, with the aid of figures wherein like structures are denoted by like reference signs, we provide detailed descriptions of exemplary embodiments of individually addressable electromagnetic array chips, electromagnetic biochips, and methods of manipulating molecules.

BRIEF DESCRIPTION OF THE DRAWINGS

FIG. 6 is a schematic diagram showing the form of a first set of conductive traces used to produce a micro-coil around each ferromagnetic core.

FIG. 7 is a schematic diagram showing the form of a second set of conductive traces used to produce a micro-coil around each ferromagnetic core.

FIG. 8 is a schematic diagram showing the form of a third set of conductive traces used to produce a micro-coil around each ferromagnetic core.

FIG. 9 is a three dimensional schematic diagram showing a micro-coil produced from a plurality of juxtaposed conductive traces of the types shown in FIGS. 6–8.

FIG. 12 is a schematic diagram showing a biochip of the present invention equipped with a fluid chamber and a window to allow optical detection.

FIG. 13 is a schematic cross-section of the biochip of FIG. 4 showing an individually addressable electromagnetic biochip.

FIG. 14 is a schematic representation showing magnetic modification of ligand or target molecules through a cleavable chemical linker.

FIG. 15 shows the use of magnetic dispensers to pick up frozen micro-particles containing ligand molecules and magnetic particles.

DETAILED DESCRIPTION OF THE PREFERRED EMBODIMENTS

The following description is provided to enable any person skilled in the art to make and use the invention and sets forth the best modes contemplated by the inventors of carrying out their invention. Various modifications, however, will remain readily apparent to those skilled in the art, since the general principles of the present invention have been defined herein specifically to provide a micro-electromagnetic device for manipulating molecules and particles to perform specific reactions.

Figure 1:
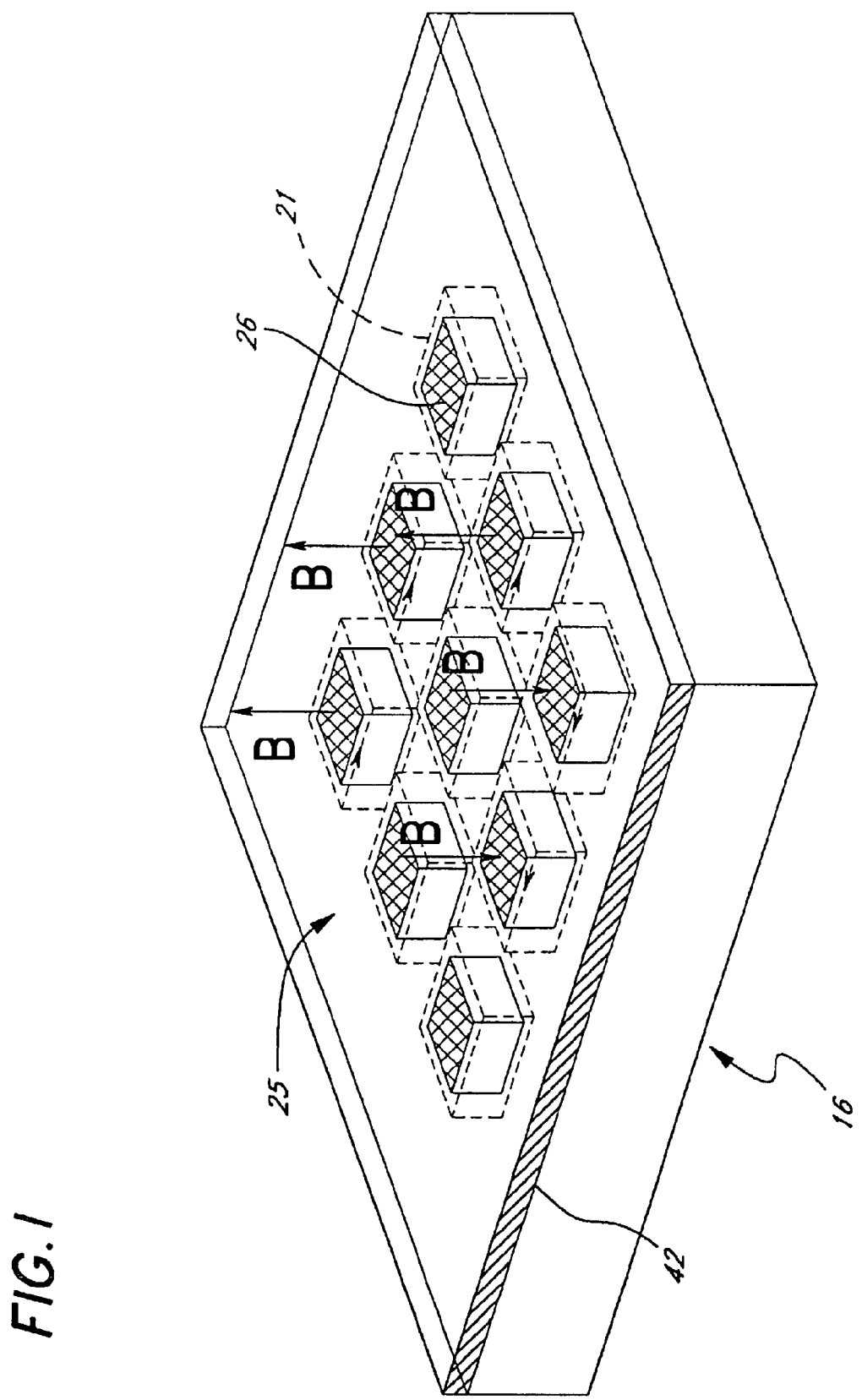
FIG. 1 shows a schematic of a chip of the present invention in three dimensional perspective with direction of the magnetic fields (vectors with B) controlled by the direction of current flow (horizontal arrowheads) in each unit.

FIG. 1 shows a three dimensional diagram of the micro-electromagnetic chip 10 of the present invention. The chip 10 comprises a plurality of micro- electromagnetic units 25 fabricated on a substrate 16, which can be made of silicon, glass, silicon-oxide, plastics, ceramics, or other solid or porous materials. In this example the electromagnetic units 25 on the chip 10 are arranged in a 3×3 array. Each electromagnetic unit 25 is capable of inducing magnetic field (B) 17 upon circulation of an electric current (horizontal arrowhead) about the unit, and can be selectively energized through a number of means. FIG. 1 shows that out of nine micro-electromagnetic units, five are energized with electric current (horizontal arrowheads) to generate the magnetic fields at their vicinities. Note that the magnetic field polarities (vertical vector arrows B) are dependent on the electric current circulation direction (e.g., clockwise or counterclockwise). A functional layer 42 (discussed below) is shown as forming an upper surface of the chip.

In FIG. 1, electromagnetic units 25 may take the form of loops of electric conductive traces (shown as a surrounding layer 21 in the figure) around a core 26 that is electrically-insulated from conductive loops 21. The loops may be of a number of geometrical shapes such as circle, spiral, square and squared-spiral. Such conductive traces having different widths and thicknesses may be fabricated on silicon substrates using different photolithographic and fabrication protocols, as known to those skilled in the art of microlithography and microfabrication (See, for example, Rai-Choudhury P. (Editor), Handbook of Microlithography, Micromachining and Microfabrication, Volume 2: Micromachining and microfabrication. SPIE Optical Engineering Press, Bellingham, Wash., USA (1997)). Such protocols may include many basic steps, for example, photolithographic mask generation, metal deposition, insulator deposition, photoresist deposition, photoresist patterning with masks and developers, metal or insulator layer patterning. Conductive traces may be made of metallic materials such as aluminum, gold, silver, tin, copper, platinum, palladium or other conductive materials such as carbon, semiconductor materials (e.g., phosphorous-doped silicon) and conductive organic polymers as well as any other materials as along as they conduct electric currents. For conducting electric current of sufficient magnitudes up to several hundred mA (milli-ampere), the conductive traces may have different cross-sectional areas up to several thousand $\mu m^2$. Thickness and width of the conductive traces may vary from 0.1 to 500 $\mu m$ and from 1 to 500 $\mu m$, respectively. For each electromagnetic unit, conductive traces may be single or multiple turns. In the case of multiple turns, multi-layer microfabrication protocols may be used to fabricate these units.

In one embodiment, selective addressing of electromagnetic units comprise electric connections between electric conductive loops and current sources through electric switches. By changing the signals applied to electric switches, the flow of electric current in the conductive loops may be turned on or off so that the electromagnetic units may be energized or switched off. In another embodiment, selective addressing of electromagnetic units may be realized through a mechanical switch that turns on or off electric current to conductive loops. In both embodiments, electromagnetic units are coupled with switches, and by controlling the switches' on/off status, various combinations of on/off status for electromagnetic units may be achieved.

To increase magnetic field strength induced by electric current in the conductive loops, magnetic cores made of ferromagnetic or ferromagnetic materials may be used. In this case, each electromagnetic unit comprises a magnetic core on the substrate, single or multiple turns of electric conductive traces about the magnetic core, means for applying electric current to the conductive traces from an electric current source. Thus, the center core of the electromagnetic unit 25 in FIG. 1 may be made of ferromagnetic material that is electrically-insulated from electric current loop. Various methods, known to those skilled in the art, may be used for depositing ferromagnetic or ferrimagnetic materials on substrates (See, for example, Ahn and Allen, "A new toroidal-meander type integrated inductor with a multilevel meander magnetic core" IEEE Transactions on Magnetics 30:73–79 (1994)).

Figure 2:
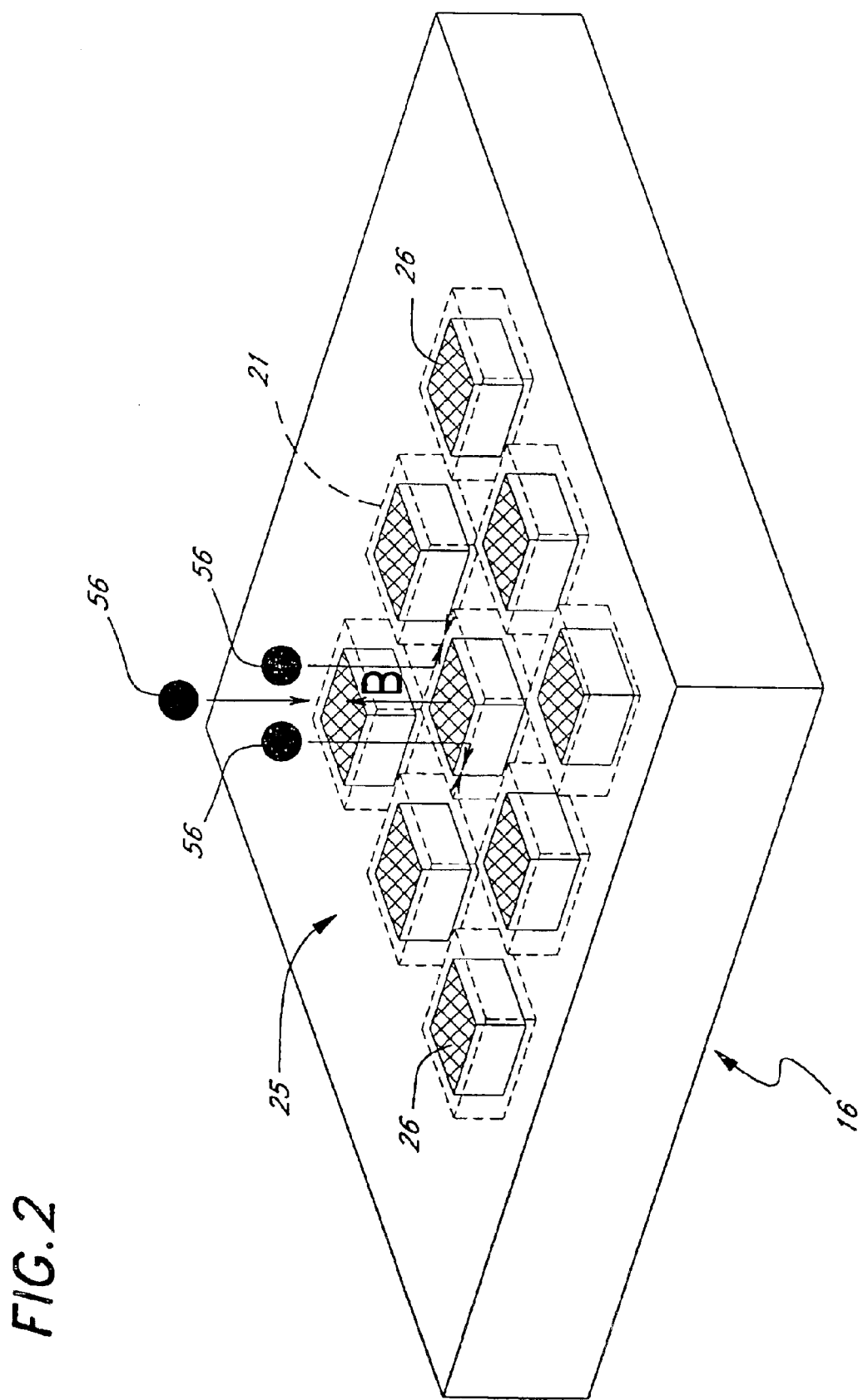
FIG. 2 shows a schematic of the biochip of FIG. 1 (functional layer omitted) showing induction of complementary magnetic fields (vectors) in paramagnetic particles.

FIG. 2 shows a schematic representation of magnetic particles 56 that are directed towards an energized electromagnetic unit 25. With electric current being applied to the unit 25, magnetic field (B) is induced in the unit's vicinity, which induces a magnetic field and magnetic forces on particles 56. The magnetic forces are dependent sensitively on the distribution of magnetic field $\overline{B}$ (and field strength $\overline{H}$). Selective addressing of electromagnetic units allows the magnetic field distribution to be controlled and changed. For example, four neighboring electromagnetic units may be energized synchronically with appropriate current flow directions to produce a magnetic quadrapole field. Magnetic field distribution may further be changed by modulating the amplitude and polarity of electric current applied to micro-electromagnetic units. The change of magnetic field distribution will in turn alter magnetic forces on magnetic particles and influence particle position, velocity and other kinetic response parameters. For example, as evidenced in Equations (2) and (3), particle velocity can be increased by increasing magnetic field strength and magnetic forces.

The functional layer 42 shown on the chip surface of FIG. 1 is used for immobilizing ligand molecules. It may be a hydrophilic or hydrophobic molecular monolayer, a hydrophilic or hydrophobic membrane, a hydrophilic or hydrophobic gel, a polymer layer, porous or non-porous materials and/or the composite of these materials. Molecular monolayer refers to single molecular layer (for example, Langmuir-Blodgett film as can be formed in a Langmuir trough). For immobilizing nucleic acid ligands, binding materials such as nitrocellulose or nylon may be used as in Southern or northern blots. Proteins and peptides can be bound by various physical (e.g., hydrophobic) or chemical approaches. For example, specific receptors such as antibodies or lectins can be incorporated into the functional layer 42 for binding ligand molecules of protein or peptide-types. Depending on the intended ligand and the assays or reactions to be carried out by the biochip, different molecules can be incorporated into the functional layer 42 for binding ligand molecules. These molecules incorporated in the functional layer 42 for binding ligand molecules are referred to as the functional groups. Examples of the functional groups include, but not limited to aldehydes, carbodiimides, succinimydyl esters, antibodies, receptors, and lectins. The functional groups also include chemical groups or molecular sites that are formed through chemical modification on the chip surface molecules. The methods of using the electromagnetic biochips 10 will be described in later sections of this description.

Figure 3:
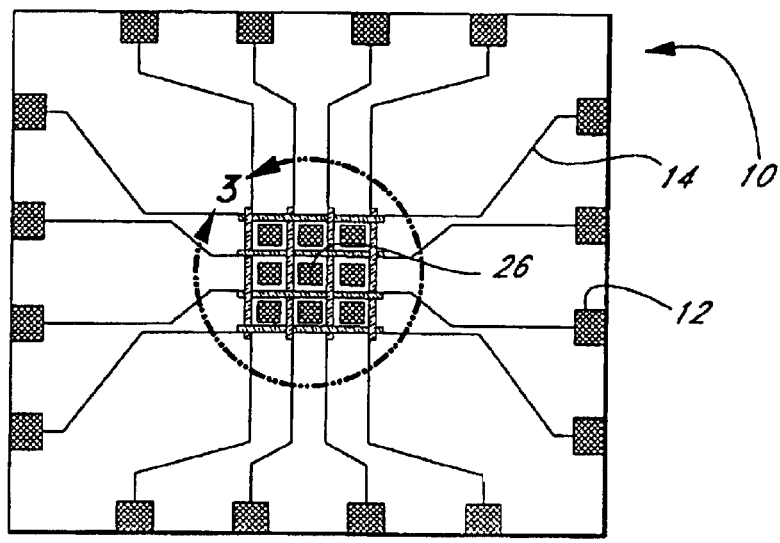
FIG. 3 is a schematic diagram showing the structures of an individually addressable micro-electromagnetic unit array chip having a column-row structure as seen from above.
Figure 4:
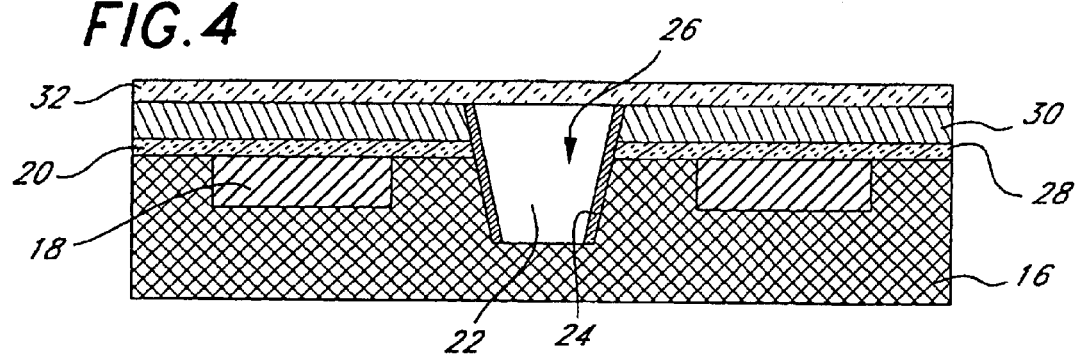
FIG. 4 shows a cross-sectional diagram of the chip of FIG. 3 taken through 2—2.

FIG. 3 shows a schematic version of the micro-electromagnetic biochip 10 according to one embodiment of the present invention as seen from above. Connection pads 12 are in electrical communication with the electromagnetic unit array by means of conductors 14. FIG. 4 shows a detailed cross-section of a single micro-electromagnetic unit. Although similar micro-electromagnetic biochips could be fabricated on a number of substrates, the illustrated embodiment is on a silicon substrate 16 that has been polished on one surface. In the following, we describe in detail the fabrication processes for the electromagnetic biochip 10 as shown in FIG. 4. These processes are for illustrative purposes only. Those skilled in the art of microfabrication may be able to readily adapt these steps or processes and modify some of the steps for producing biochips with the same structures as shown in FIG. 4.

In one example conductive regions are produced by surface diffusion (doping) with phosphorus to yield an electrical sheet-resistance of 2–10 Ω/square. Insulating layers of $SiO_2$ having a thickness between, for example, 1000 and 8000 Å are produced by thermal decomposition as detailed below. Based on the requirements of dimensions and array density for the micro-electromagnetic unit array chip, parallel conductive traces 18 are photolithographically formed on the substrate 16 by phosphorus injection. The surface density of phosphorus diffusion is adjusted to give a sheet-resistance less than or equal 10 Ω/square for conductive trace 18. Because the traces 18 are formed within the substrate 16, they have no relief and are not raised above the polished surface of the substrate 16. After forming the first layer of conductive traces 20, an $SiO_2$ insulating layer with a thickness of 2000–4000 Å is grown on the surface of the substrate 16 by placing the chip into a high temperature oven (e.g. 1000° C.). A first insulating layer of $SiO_2$ 20 is thereby formed on the substrate 16 covering the first layer of conductive traces 18.

Using photolithography, potential cavities for electroplating are laid out at designated areas between the first conductive traces 18. For example, an array of 10 $\mu$m deep electroplating cavities 22 is etched by applying a KOH solution (30% w/w) to the silicon substrate 16. In cross-section each of the electroplating cavities 22 should have trapezoidal shape with its smaller parallel face towards the bottom surface of the substrate 16. An additional $SiO_2$ layer 24 with thickness of about 5000 Å is then deposited over the electroplating cavities 22, and the $SiO_2$ layer at the bottom of electroplating cavities 22 is removed by photoetching.

The cavities 22 are then filled with ferromagnetic material to create magnetic cores. This is accomplished by first placing the substrate 16 into a $NiSO_4$ solution (200–400 g/l) and heated to between 400 and 600° C. for 30 minutes under nitrogen gas, so that a seed layer of nickel with thickness of about 1 $\mu$m is formed at the bottom of the electroplating cavities 22.

A magnetic-core 26 for each cavity 22 can be formed by electroplating according to the following steps and conditions: (1). in $Fe/FeCl_2$ solution (ratio 200:500 g/l) at 20–40° C.; (2). in FeNi/NiSO4 solution (200:400 g/l) at 30–60° C.; (3). in $FeCl_2$ solution (10–60 g/l) at 30–60° C. Thus, an array of magnetic-core 26 is formed on the substrate 16, where the top surface of magnetic-cores 26 is higher than the top surface of the first $SiO_2$ insulation layer 20. Magnetic core 26 can be electroplated according to other conditions and steps to have compositions. For example, to obtain a nickel (81%)-iron (19%) Permalloy, an electroplating solution may have the following components: $NiSO_4.6H_2O$ (200 g/l), $FeSO_4.7H_2O$ (8 g/l), $NiCl_2.6H_2O$ (5 g/l), $H_3BO_3$ (25 g/l) and sucrose (3 g/l). An electric current density of ~5 mA/cm$^2$ may be used to have an electroplating rate ~0.3 $\mu$m/minute. Other details of electroplating conditions may be found in various references (e.g., Romankiw and O'Sullivan, "Plating techniques" in Handbook of Microlithography, Micromachining and Microfabrication, Volume 2: Micromachining and microfabrication, Editor: Rai-Choudhury P., SPIE Optical Engineering Press, Bellingham, Wash., USA (1997)).

After forming the array of magnetic-cores 26, a $Si_3N_4$ insulation layer 28 with thickness of about 5000 Å is deposited by thermal decomposition at a temperature of 200–300° C. over the magnetic-cores 26 and the first insulating layer 20. Next a conductive layer of aluminum with thickness of about 1.2 $\mu$m is sputtered onto the surface of $Si_3N_4$ 28 insulation layer. A second series of conductive traces 30, perpendicular to the first series of conductive traces 18, is formed between the magnetic-cores 26 by photolithography and wet etching of the aluminum. Therefore, a micro-electromagnetic unit array is formed that consists of the array of magnetic-cores and a two dimensional network of conductive traces. The top surface of the aluminum conductive traces 30 may be even with or higher than the top surface of magnetic-cores 26. Finally, a second $Si_3N_4$ insulation layer 32 with thickness of about 4000 Å is deposited on the surface of the aluminum conductive traces 30 at about 300° C. Then, the insulating materials over the ends of the first conductive traces 18 and over the ends of the second conductive traces 30 are removed by dry etching method, so that the ends of conductive traces can be connected by the conductors 14 to the pads 12 which may then be connected to external electric circuits.

Figure 5:
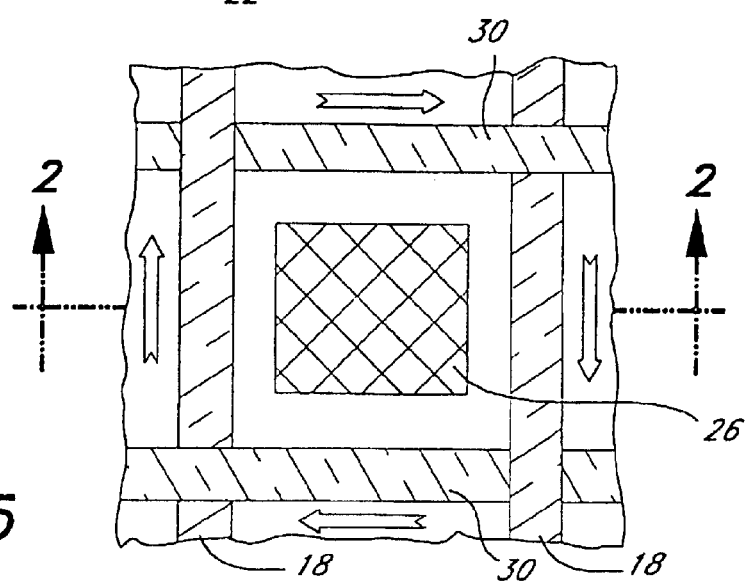
FIG. 5 is a schematic diagram of a magnetic core from above showing the electrical current flow for turning on (magnetizing) a micro-electromagnetic unit.

The conductive traces 18 and 30 of the micro-electromagnetic unit array are powered by a DC current source. Each individual magnetic unit of the micro-electromagnetic unit array is controlled by selectively energizing different conductive traces 18, 30. As shown in FIG. 5, the magnetic field is produced around the selected unit by selecting the direction of electric current through the surrounding traces to form a closed current loop around the magnetic-core 26. That is, to magnetize a core in a given column, the traces 18 on either side of that column are energized so that an electric current will flow up one side of the column and down the other. This current flow will have the effect of magnetizing all of the units in the column to some extent. However, any predetermined unit in the column is also a member of one of the rows of units. By causing an electric current to flow in the traces 30 on either side of that row, all of the members of the row will be magnetized to some extent; however, the selected unit, as shown in FIG. 5, will have a current flowing around all of its sides (from the row current and from the column current). This results in the selected unit being magnetized with twice the strength of the other units. The polarity of the induced magnetic field depends on the direction (e.g., clockwise or counterclockwise) of current flow (arrows) in the loop.

It is possible to increase the magnetic field strength of the selected unit by making a structure where the selected unit is surrounded by more than one "turn" of conductive trace (e.g., as in making a miniature coil), Single or multiple two dimensional conductive trace networks may be added on the top of insulation layer 32 by similar method that creating the conductive traces 18 and 30. Each network consists of two layers of conductive traces that are insulated from each other and whose position coincides with the conductive traces 18 and 30, respectively.

The magnetic strength of the selected unit can be increased further by using microfabrication methods to actually produce micro-coils surrounding each core. For a given current flow the magnetic force developed by the core is proportional to the number of turns in the miniature coil. A large number of methods, readily apparent to one of ordinary skill in the art of microfabrication and micromachining, can be used to fabricate such micro-coils. The following approach has be used by the present inventors, but the invention is not limited to this method alone. The micro-coils are fabricated from conductive traces as mentioned above. Again, conductive layers of doped silicon and metal (e.g., aluminum) are used alternatingly. Unlike the example given above, the conductive layers are connected in the vertical dimension. In fabricating the first layer of conductive traces 18, instead of having straight traces run on either side of a column of cores 26 each trace 34' runs almost completely around each core as shown in FIG. 6. This trace can conveniently be produced by the phosphorous diffusion process described in relation to the column traces 18. This trace is covered by an insulating layer 20 as in the simpler micro-electromagnetic array described above. A second micro-coil trace 36 is deposited on top of the insulating layer 20 as is shown in FIG. 7. Preferably this layer is fabricated by sputtering and etching as in the case of the row traces 30 described above. Prior to the sputtering process, the insulating layer 20 is etched at vertical interconnect points 35 so that there will be a vertical connection between the micro-coil traces 34 and 36. The interconnect point 35 should be arranged so it coincides with the endpoint of the first micro-coil trace 34 and the starting-point of the second micro-coil trace 36. It will be apparent that the trace 36 of FIG. 7 actually has two interconnect points (at the start and at the end of the loop). For clarity these are differentiated as 35 and 35'. The second layer of micro-coil traces 36 are covered by an additional insulating layer 20. The above processes are repeated to deposit a third layer of micro-coil traces 38 as shown in FIG. 8. These traces 38 like the first micro-coil traces 34 lead out of the array to row connections with conductors 14 and pads 12 (not shown).

The point is that each trace layer effectively adds a single conductor turn to the micro-coil. Each micro-coil consists of a starting "column" layer 34 and an ending "row" layer 38. In between the column and row layer there can be a variable number of "loop" layers 36 depending on the desired number of turns in the micro-coil. Note that the "gap" 40 of each successive layer is offset slightly. Such offset is necessary to ensure that the interconnect points 35, 35' always coincide with the end-point of the conductive trace loop in one layer and the starting point of the conductive trace loop in the successive layer. This concept is illustrated in FIG. 9 which illustrates a three dimensional view of a multi-layered micro-coil containing a plurality of intermediate layers 36.

Alternatively, some of the micro-coil trace layers can be implemented with doped silicon as in the initial column traces 18. This choice is a matter of design preference and may alter the profile of the device. One way of using doped silicon is to deposit a layer of amorphous silicon above the insulating layer 20 and then create the illustrated trace patterns by photolithographic directed doping. After all the micro-coil layers except the final "row" layer have been fabricated, the cavities 22 are created by etching and the ferromagnetic cores 26 are formed by electroplating. Then the final micro-coil "row" layer 38 and the insulating capping layer 32 are created to complete the structure. The advantage of the micro-coils is that a stronger magnetic force (proportional to the number of micro-coil "turns") is developed by each magnetic core. Further when a selected core is magnetized by selecting a given column and row, the other cores may be magnetized only to a very small extent or not at all.

Figure 10:
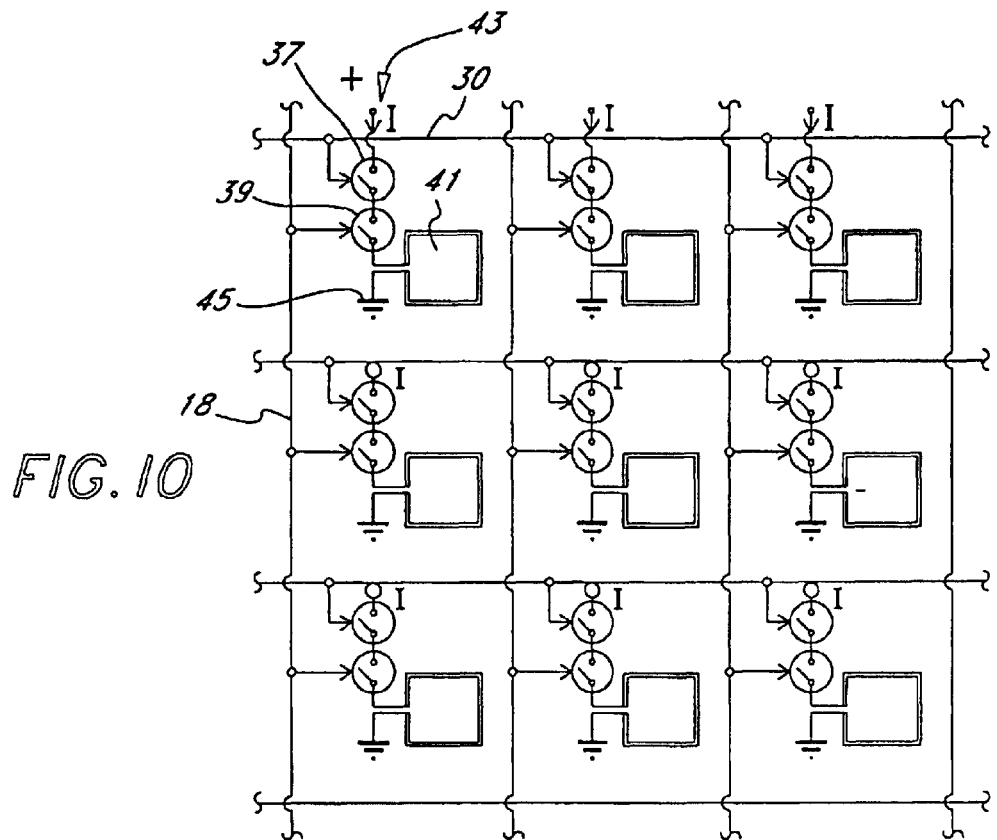
FIG. 10 is a schematic diagram showing the principle of addressing individual micro-electromagnetic units by using electric switches. Each unit is connected to the current source and the common ground through two electric switches connected in series. The two switches are controlled by electric signals applied to the rows and columns of the electric conductive lines.
Figures 11A, 11B:
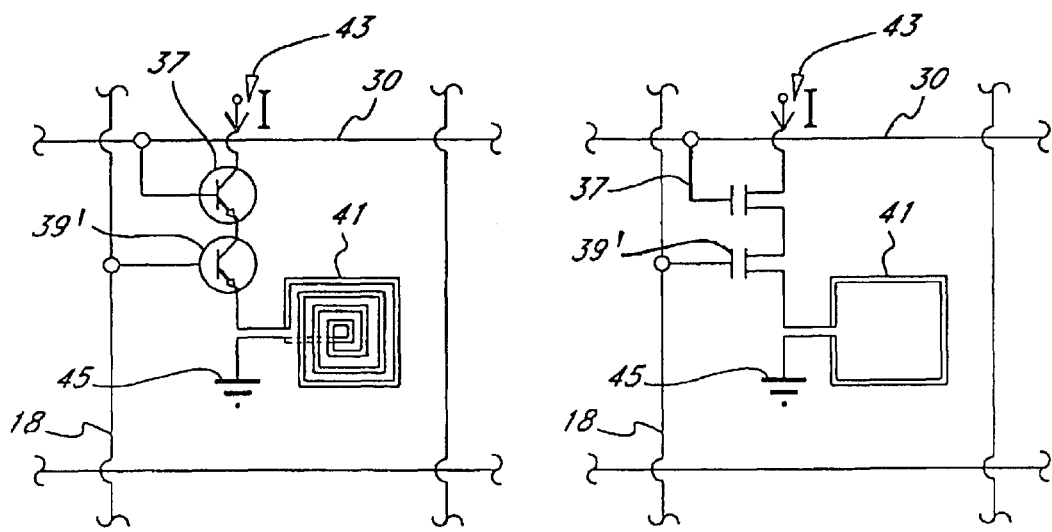
FIG. 11a shows the schematic of FIG. 10 wherein each electric switch is a bipolar transistor.
FIG. 11b shows the schematic of FIG. 10 wherein each electric switch is a MOSFET (Metal-Oxide-Semiconductor-Field-Effect-Transistor).

FIG. 10 shows the principle of addressing individual micro-electromagnetic units by using electric switches. In the figure, each unit 41 is connected to the common electric current source 43 and the common ground 45 (i.e. a current sink) through two electric switches 37 and 39 in series. The switch 37 is controlled by electric signals applied to the rows 30 of the electric conductive lines. The switch 39 is controlled by electric signals applied to the columns 18 of the electric conductive lines. An individual unit 41 is switched on (i.e. there is a current flow from the current source 43 to the unit 41 and through the unit to the ground 45) when and only when both electric switches are turned on. An electric switch can be, for example, a bipolar transistor as shown in FIG. 11a, or a MOSFET (Metal-Oxide-Semiconductor Field-Effect-Transistor) as shown in FIG. 11b. Thus, the electric potentials applied to the base of the bipolar transistor or to the gate of the MOSFET determines the on/off status of these electric switches. The unit 41 is shown as a square loop of single turn in FIG. 10 and 11b, and as a squared-spiral loop of multiple turns in FIG. 11. These transistors can be readily fabricated using the similar fabrication techniques to those used for producing the micro-electromagnetic array described above and can be integrated together with the electric conductive loops on a same substrate. The current source 43 and common ground 45 may take the forms of two separate conductive layers in the final structure and are connected to outputs of a DC power supply. The current going through a micro-electromagnetic unit will be equal to the voltage from the power supply divided by the total resistance of the current-flowing circuit (including the resistance of the on-state electric switches and of the conductive loops).

In the foregoing examples, the substrate material is silicon, but other materials, such as glass, silicon dioxide, ceramics or even plastics, etc., may also be used as substrates. The substrate can be made of porous or non-porous materials. Similarly, the materials for the insulation layers 20, 28, and 32 are not limited to the materials used in this example, but may be plastics, glass, photoresist, rubber, ceramics etc. The conductive traces may be aluminum, gold, tin, copper, platinum, palladium, carbon, semiconductor materials or composite of above materials. Similarly, other configurations of the conductive traces and micro-coils are possible. The illustrated method of producing a magnetic-core by electroplating is merely an example. Magnetic cores can be deposited in proper relation to conductive traces (micro-coils) by means of electron beam evaporation, sputtering or other deposition techniques well-known to those of skill in the art of microfabrication and micromachining. Furthermore, magnetic cores can be fabricated from a wide range of ferromagnetic or ferrimagnetic materials deposited by electron-beam evaporation, sputtering and other such methods. The present invention comprises individually controllable micro-electromagnetic units on a substrate. Using such chips, directed manipulation of biomolecules, chemical reagents and drug molecules is made possible through the application of magnetic fields.

After the micro-electromagnetic array chips are fabricated, the surface of top insulation layer 32 may be chemically modified or may be coated with a thin film layer. This layer is called functional layer 42, which is used for immobilizing ligand molecules. Illustrated in FIG. 13, the functional layer 42 may be hydrophilic or hydrophobic molecular monolayer, a hydrophilic or hydrophobic membrane, a hydrophilic or hydrophobic gel, a polymer layer, or the composite of these materials, as described in the section related to FIG. 3. The functional layer may be made of porous or non-porous materials. The functional layer 42 may incorporate specific molecules such as antibodies for binding ligand molecules, depending on the intended ligand and the assays or reactions to be carried out on the biochip. These molecules incorporated in the functional layer for attaching or binding ligand molecules are referred to as functional groups. For immobilizing nucleic acid ligands binding materials such as nitrocellulose or nylon, polylysine, agarose gel, hydrogel, acrylamide gel as used in Southern or northern blots may be used as functional layers. For immobilizing proteins and peptides, antibodies or other protein molecules may be incorporated into the functional layer 42 and used as the functional groups.

After the formation of functional layer, the ligand molecules 44 that have been magnetically modified or loaded (as explained below) can be immobilized onto the functional layer 42 by reacting with different function binding moiety provided. In FIG. 13, a "lock in key" reaction such as that characteristic of an antibody is illustrated, but clearly the immobilization is not limited to this type of reaction. The precise site of immobilization on the functional layer 42 is controlled by the magnetic fields generated by the electromagnetic units. That is, in most cases the ligand will be immobilized immediately above a unit if a single electromagnetic core 26 is magnetized. As is well-known, the polarity of an electromagnet is controlled by the direction of current flow about the electromagnet. Depending on the direction of current flow (clockwise or counterclockwise) the units will either have North poles or South poles pointing towards the functional layer 42. Thus, when two adjacent electromagnetic units are energized to have either the same polarity or opposite polarities, the superimposition of the magnetic fields due to the two electromagnetic units will determine the magnetic forces acting on magnetically-modified ligands and determine where the ligands will be immobilized. It is possible to energize neighboring electromagnetic units in a synchronized way to alter magnetic field distribution and to change the forces acting on magnetically-modified molecules. In order to hold the affinity ligands, reagents and reactants, and to allow for addition and removal of the liquids, a fluid chamber 46 is constructed around the chip 10. A diagram of such a chambered biochip is shown in FIG. 12.121212 The chip 10 is enclosed in a suitable chamber 46 of plastic or other materials. Inlets and outlets 48 are provided for liquid flow. A quartz coverslip 50 (glass or other optically transparent material can be used; quartz is a good material for ultra-violet measurements) is sealed to the top of the chamber 46 with silicone rubber or other suitable material. The coverslip 50 allows optical detection of ligands and reaction products within the device. Alternatively, if non-optical detection methods are employed, the chamber top 50 does not have to use optically-transparent materials.

Thus, we have completed the description of the construction of examples of individually addressable micro-electromagnetic biochips according to the present invention. The precise structure and fabrication of the individual magnetic cores can be altered without departing from the basic invention disclosed herein.

FIGS. 13 through 23 illustrate methods for using an electromagnetic biochip shown in FIG. 3 to manipulating molecules, of chemical, biological, pharmaceutical or other types, according to the present invention. These methods include following steps:

a. Constructing an individually addressable micro-electromagnetic array chip 10 shown in FIG. 3.

b. Forming a functional layer 42 on to the surface of the above chip. This functional layer is used for immobilizing ligand molecules.

As described above this layer 42 may be formed by direct chemical modification of the surface of the insulation layer 32 or by polymer coating or by introducing affinity molecules or reactive functional groups. The layer may be a functional hydrophilic or hydrophobic molecular monolayer, hydrophilic or hydrophobic membrane, functional hydrophilic/hydrophobic gel, polymer layer, porous or non-porous layer or the composite of these materials.

c. Magnetic modification or loading of ligand molecules that will be subsequently immobilized on the functional layer 42.

d. Controlling electric current in individual traces 18, 30 to create magnetic fields around desired micro-electromagnetic units so that the magnetically modified or loaded ligand molecules are drawn to and immobilized at desired micro-locations on the functional layer 42 to form affinity binding regions required by various assays on the chip surfaces.

There are various methods for manipulating and immobilizing the ligand molecules at specific regions through the application of magnetic field. As shown in FIG. 14, the ligand molecules 44 may be linked onto a paramagnetic bead 56 through a cleavable linker 54. Thus, the ligand molecules can be transported, manipulated and released at specific regions by taking advantage of forces acting on the paramagnetic beads 56 due to magnetic field generated by the electromagnetic biochip. The paramagnetic microbeads 56 may range in size from less than 100 nm to more than 100 $\mu$m. They can be manufactured by methods known in the art or can be purchased from Companies such as Dynal or Seradyn. The cleavable linkers 54 may be photocleavable, heat cleavable, enzyme cleavable or cleavable by a specific chemical reaction. The connection between the cleavable linker 54 and the paramagnetic micro-bead 56 may be made by a covalent bond or by means of molecular affinity (e.g., antibody-antigen or lectin-sugar) between an end functional group 52 of the cleavable linker and a receptor group 58 of paramagnetic micro-bead 56.

For example, the overall assembly may be as follows:
Ligand (44)-cleavable linker (54)-biotin (52)-streptavidin (58)-paramagnetic microbead (56)

Here, biotin-streptavidin binding serves as the connection between cleavable linker and paramagnetic microbeads. Such a molecular assembly can be used as a general format for modifying any ligand molecules with paramagnetic microbeads using the following steps. First, streptavidin molecules are coupled to the surfaces of paramagnetic microbeads using the methods known to those skilled in the art (typically, paramagnetic microbeads have a surface of a polystyrene layer having carboxyl or amino groups). Alternatively, streptavidin-coated paramagnetic microbeads may be purchased from manufacturers. Secondly, "cleavable linker-biotin" molecular-complexes are prepared. These two steps are applicable to magnetic modification of any types of ligand molecules. Thirdly, specific ligand molecules are coupled to cleavable linkers through, for example, covalent bonding. Finally, the overall molecular assembly is formed by incubating streptavidin-coated paramagnetic beads with "ligand-cleavable linker-biotin" molecular complexes to allow biotin-streptavidin binding reaction to take place.

For immobilizing ligand molecules, the magnetic field generated by energized magnetic units will exert magnetic forces on the paramagnetic microbead 56 that will bring the overall molecular assembly into contact with the surface of the biochip above the energized electromagnetic unit. The cleavable linker can then be cleaved so that the microbeads 56 can be removed after the unit is switched off. As explained below, a fluid wash or externally applied magnetic force can be used to remove all the microbeads leaving the ligand molecules immobilized on the functional layer 42.

Figure 16:
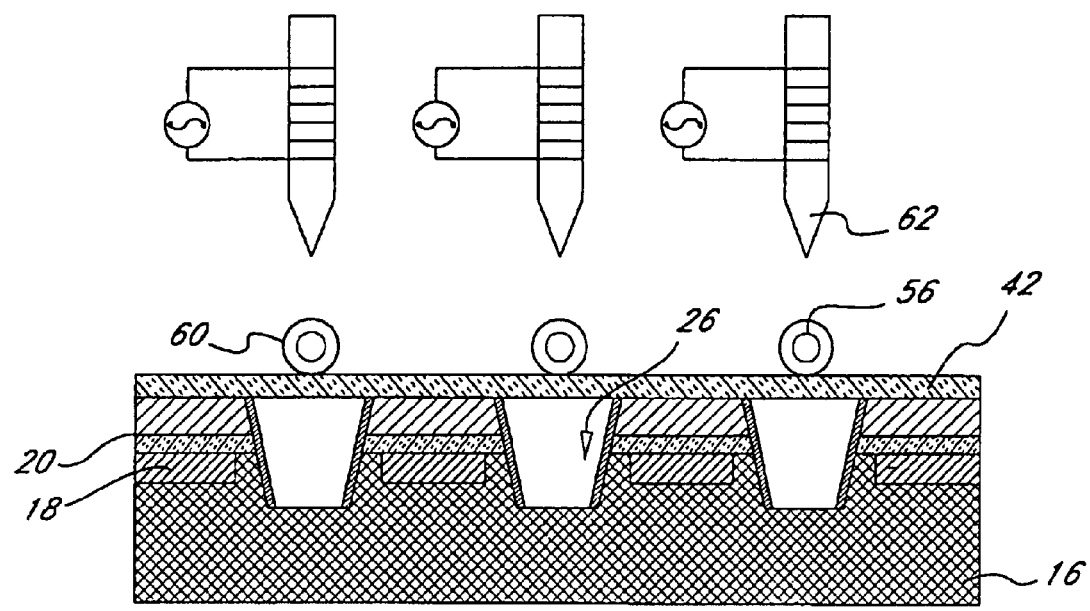
FIG. 16 shows the release of the frozen micro-particles of FIG. 15 on the surface of a biochip of the present invention.
Figure 17:
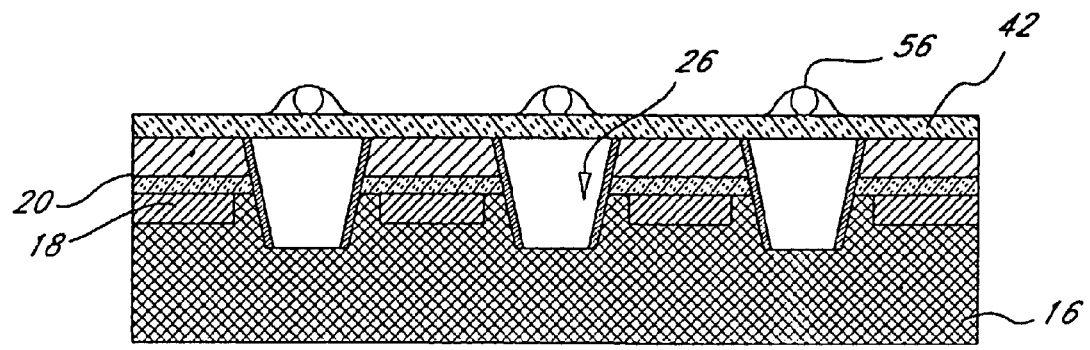
FIG. 17 shows the melting of the frozen micro-particles (containing ligand molecules and magnetic particles) of FIG. 15.
Figure 18:
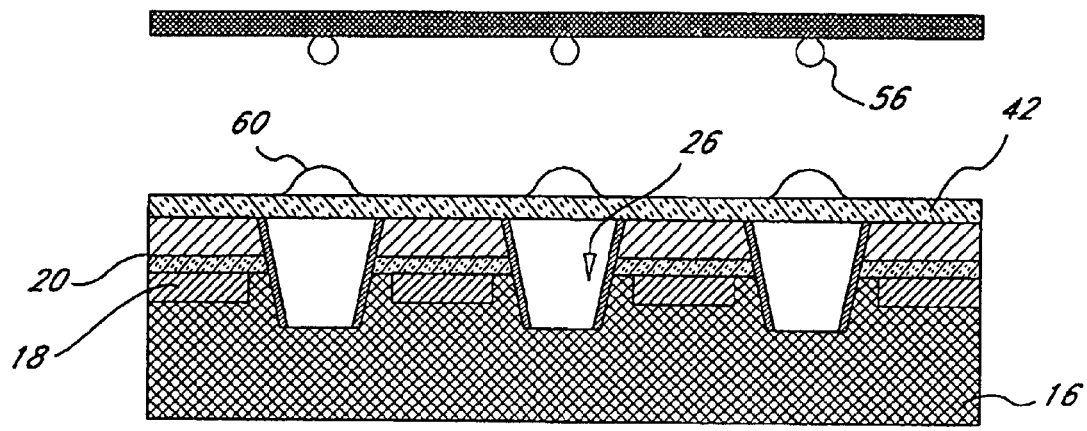
FIG. 18 shows the removal of magnetic particles from the ligand molecules of FIG. 17.

Another method for magnetically loading ligands is to mix the solution containing ligand with paramagnetic microbeads and then rapidly freeze them to form solid microparticles 60 (usually less than one millimeter in diameter) containing the ligands and paramagnetic micro-beads. The solidified micro-particles 60 prepared from different samples may be stored in a freezer for future use. Directed transportation of such solidified micro-particles to the chip can be achieved by a three-dimensional precision robotic arm equipped with a specially designed magnetic microparticle dispenser 62 (an electromagnetic probe). After the solidified micro-particles are carried to predetermined positions above the designated region on the chip, the microparticles are released and immobilized (FIGS. 15 and 16) by controlling the electric current at the designated microelectromagnetic unit so that the magnetic field on the chip region is stronger than the field on dispenser head 62. Thus, the solidified micro-particles 60 are released onto the functional layer 42 of the chip 10 at the designated regions (FIG. 16). After melting the solid micro-particles 60, the ligand molecules are immobilized on the designated chip regions (FIG. 17). Such steps have additional advantages as follows: the cross contamination between ligand molecules by the magnetic dispenser 62 is reduced to minimum without cleaning the dispenser head after each delivery. After the immobilization of ligand molecules on the chip surfaces is complete, the magnetic microbeads 56 may be removed from the chip by additional magnetic forces above the chip surface or by fluidic wash (FIG. 18).

The affinity binding area on each micro-electromagnetic unit on the chip may have characteristic dimensions between 0.1 $\mu$m to 5 mm (width and length for rectangular shape, or diameter for circle shape). The size of the binding area depends on the dimensions of each magnetic-core 26 and whether multiple cores are energized and the polarities of the energized cores. The exact dimensions of the affinity binding areas can also be altered by controlling the functional layer 42—e.g., the functional layer 42 can be deposited under photolithographic control (as opposed uniformly covering the chip).

e. Target molecules 62 are labeled (e.g., with a fluorophore 64) and connected onto magnetic microbeads 56.

To use the individually addressable microelectromagnetic chips described in this invention to manipulate the target molecules 62, these molecules need first to be magnetically modified.

There are also various methods to magnetically modify the target molecules. For example, the target molecules 62 may be linked onto a paramagnetic bead 56 through a cleavable linker 54 so that the target molecules may be manipulated and moved to the target area by applying magnetic fields. The connection of cleavable linker 54 and a paramagnetic microbead 56 may be achieved by covalent bonds or by affinity between the end functional group 52 of the cleavable linker and the functional group or receptor 56 of paramagnetic microbead. For example, the connection may be structures as (FIG. 19):

Tag (64)-Target molecule (62)-cleavable linker-biotin-streptavidin-microbead (56)

Figure 21:
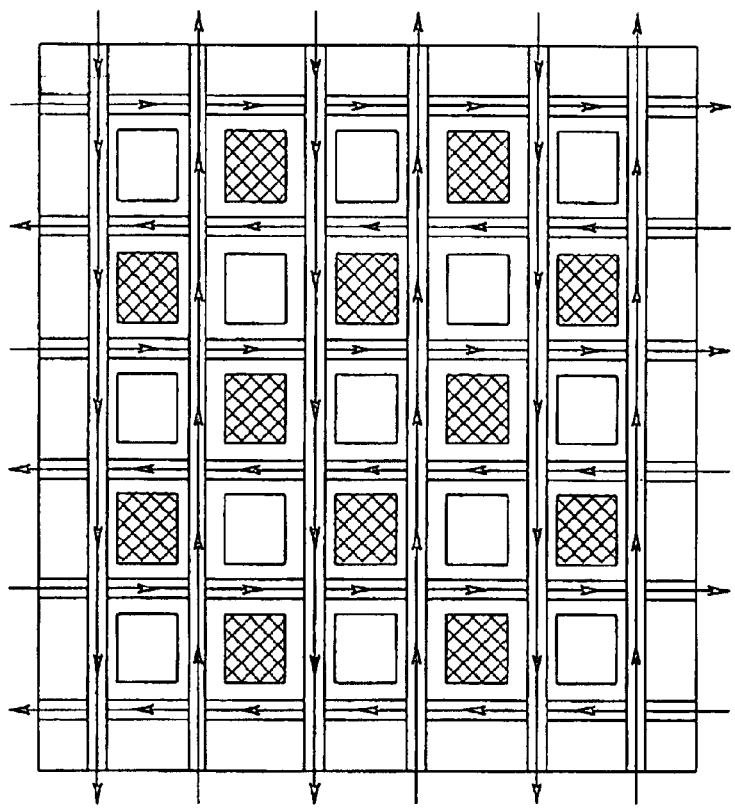
FIG. 21 shows a different pattern of electric current flow through the conductive traces of an electromagnetic chip. This current flow pattern allows for energizing micro-electromagnetic units that are NOT energized in FIG. 20.
Figure 22:
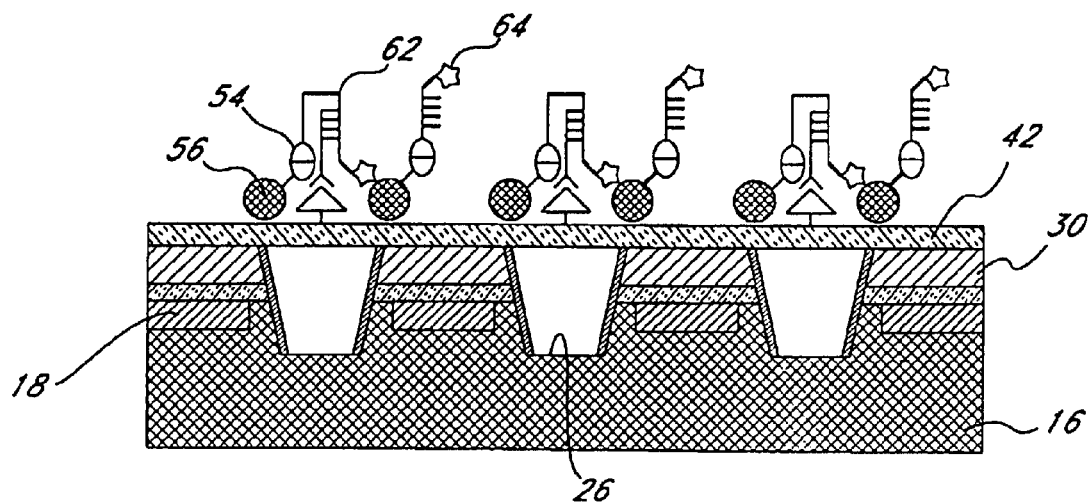
FIG. 22 shows the immobilization of magnetically-modified target molecules on the electromagnetic chip surface.

Such assembly can be formed using the similar procedures to those described above for forming "ligand-paramagnetic microbead" assembly.

f. The target molecules 62 that have been linked to paramagnetic beads 56 are placed in the fluidic chamber 46 and are brought into contact with the ligand molecules 44 immobilized on biochip surfaces by controlling magnetic fields.

g. In the case of column/row unit arrays, energizing micro-electromagnetic units using the electric current flowing patterns illustrated in FIGS. 20 and 21 allows alternative turn-on and turn-off of magnetic fields at the microelectromagnetic units. 13 out of 25 units are energized in FIG. 20 while other 12 units are energized in FIG. 21. Thus, the magnetic field generated at individual microelectromagnetic units attracts the magnetically-modified target molecules 62 and moves them close to the designated ligand affinity binding regions. By changing the magnetic patterns sequentially, every electromagnetic unit can attract and concentrate the target molecules 62 from its vicinity in solutions. Therefore, affinity binding reactions between target molecules 62 and the ligand molecules 44 are brought about (FIG. 22).

Figure 19:
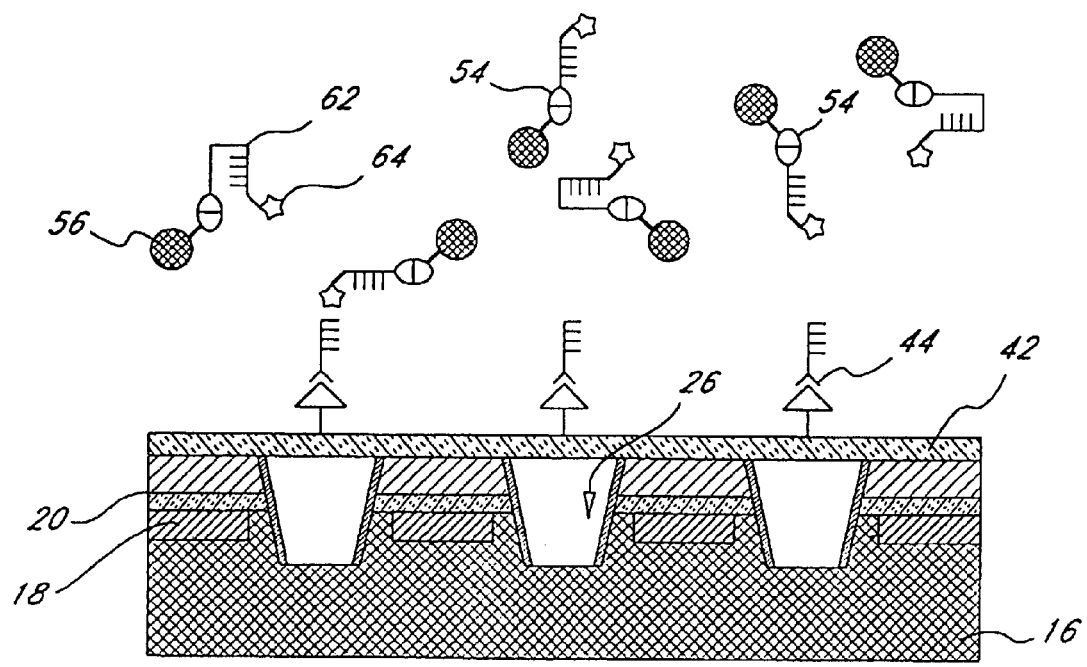
FIG. 19 shows the random movement of magnetically-modified target molecules above the surface of a biochip of the present invention following melting of the frozen microparticles.
Figure 20:
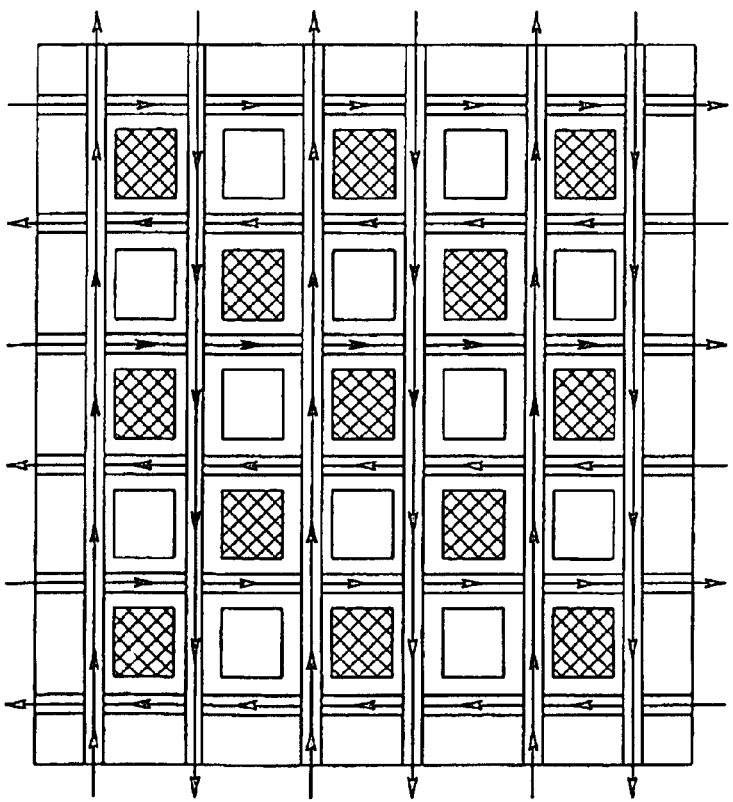
FIG. 20 shows a pattern of electric current flow through the conductive traces of an electromagnetic chip for energizing a group of micro-electromagnetic units (i.e., magnetizing a group of magnetic cores); note that the energized units (shaded) show a continuous loop of current around the unit.
Figure 23:
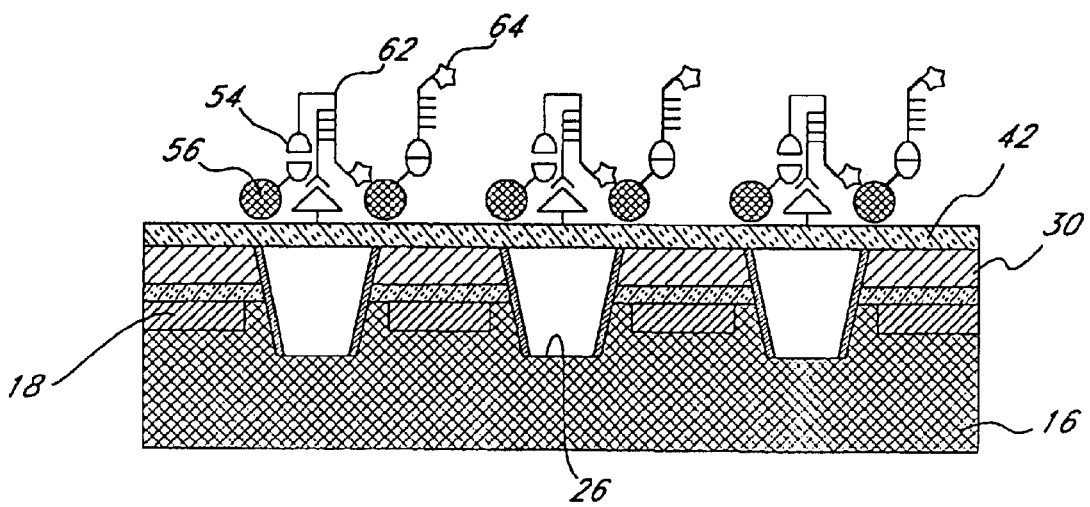
FIG. 23 shows a schematic representation of cleaving the magnetic particles from the target molecules after the target molecules have undergone reaction with ligands at the surface of the biochip of the present invention.

When the magnetically-modified target molecules 62 are introduced onto the electromagnetic biochips for analyses, the motion of the target molecules 62 is at first controlled by random diffusion (FIG. 19). The directed movement of the sample molecules to all the micro-electromagnetic units is achieved by applying magnetic fields through alternatively turn-on and turn-off of the magnetic field at all the units as illustrated in FIGS. 20 and 21. According to the specific assays, directed movement of target molecules 62 to one or a number of selected micro-electromagnetic units can also be achieved by selectively switching on these units. Under the influence of the magnetic field generated by the selectively-addressed micro-electromagnetic unit, the magnetically-modified target molecules 62 can be caused to rapidly move towards the biochip surface, and to undergo the affinity binding reactions (or other reactions) with the ligand molecules 44 immobilized in the designated unit regions. (FIG. 22).

h. In a final step, the target molecules 62 (or their reaction products) are separated from the magnetic microbeads 56, which are then removed. Separation of target molecules 62 from magnetic microbeads 56 can be accomplished by photocleavage, enzymatic digestion, chemical cleavage, etc. of the cleavable linker 54 between target molecule 62 and microbeads 56 (FIG. 23). The magnetic microbeads 56 can be removed from the chip surface by the application of additional magnetic forces above the chip (not effective with a closed fluid chamber 46) or may be washed away by liquid flowing through the chamber 46.

In above-mentioned method, the ligands and target molecules can be any type of molecule (e.g., biological, pharmaceutical, or any other chemical entity). The methods in this invention can be applied for determination of specific DNA sequences by hybridization, binding assays of antigen-antibody reactions and drug screening (e.g., binding of drug molecules or potential drug compounds to specific receptors). For example, a library of candidate drug compounds could be prepared as ligand molecules and localized at predetermined locations on the functional layer 42. Biological receptors could be isolated from cells or produced by genetic engineering methods and fluorescently labeled. The receptors are then either specifically localized on the functional layer 42 to correspond with candidate compounds. After a washing step, any candidate compounds that "lit up" with the label is a compound that shows promise of interacting with the biological receptor. Therefore, this invention can be applied to perform controlled biochemical reactions, biochemical detection and clinical diagnostic tests. Also special organic reactions to assemble complex large molecules can also be achieved.

When the above-described methods are used for DNA hybridization, after step h, non-specifically hybridized DNA molecules can be removed by stringent control of the binding conditions, such as hybridization buffer, temperature etc. This leaves the DNA molecules showing high affinity left hybridized to the ligand molecules where they can be detected by fluorescence, etc.

When the above-described methods are used for antigen-antibody interaction, after step h, non-specifically bound antigen or antibody molecules can be removed by stringent buffer washing conditions and whereas the specific bound antigen or antibody molecules remain on the affinity binding area.

When the above-described methods are used for biological analyses, the detection and quantification of the analytical results may be obtained using several detection methods, such as optical signals (either through measurement of absorbance or fluorescence), chemiluminescent or electro-chemiluminescent detection, electrochemical detection, and detection of radioactive labels. Optical detection can be accomplished by detecting the fluorophore 64 carried by the target molecules, which is excited by laser light source. Another optical detection method utilizes fluorophore-tagged probes or secondary antibody which specifically bind to the target molecules, and then the florescence are induced by laser light source. Fluorescence resonance energy transfer can also be used to detect the close proximity of the ligand 44 to the target molecule 62. The details about fluorescence resonance energy transfer can be found in the article by Ju et al., "Fluorescence energy transfer dye-labeled primers for DNA sequencing and analysis" in *Proc. Natl. Acad. Sci.* USA, 92:4347–4351, and in references titled in the article. The following is a practical example for controlled DNA molecule operation that uses the methods of this invention.

First, an individually addressable micro-electromagnetic array chip is constructed according to the methods described in this invention. The surface of the chip is coated with a layer of high molecular polymer for DNA probe immobilization.

The paramagnetic microbeads are added to the solution that contains DNA probes and the mixtures are then quickly frozen to form solid micro-particles. The micro-particles are transported to the designated regions (micro-electromagnetic units) of the biochip using a precision robot arm equipped with a magnetic dispenser 62. A plurality of different probes are immobilized at a plurality of different regions (one probe per region). Potentially each chip could have as many different probes as there are individual magnetic units on the chip. A stronger magnetic field than that of the magnetic dispenser is generated on the unit of the biochip by connecting electric currents to the selected units. The probe mixed micro-particles are released on the functional layer of the specific units on the biochip. When the solid microparticles melt, DNA probes in the liquid become immobilized at the designated unit (region) on the biochip. Then the free magnetic microbeads are removed by an additional magnetic field applied above the surface of the biochip or removed by a fluid wash. Thus affinity binding regions are formed on the biochip surface.

The target DNA molecules are labeled (e.g., with a fluorophore or radioactive probe) and are linked to the one-ends of photocleavable linker molecules. On the other end of the linkers there are biotin molecules. Streptavidin molecules are immobilized on the surface of the magnetic microbeads. Then, solutions containing target DNA-linker-biotin complexes and streptavidin-coated magnetic microbeads are mixed together. The target DNA molecules are linked to magnetic microbeads by biotin-streptavidin interaction.

DNA target-photocleavable linker-biotin-streptavidin-magnetic microbeads.

The solution containing magnetically-modified target DNA molecules is then placed in the liquid chamber on the biochip. The micro-electromagnetic units are alternatively energized to produce magnetic fields in each unit on the chip. The target DNA molecules that are modified by magnetic microbeads are moved to the probe DNA molecules that have been immobilized on the chip surfaces. IF all the electromagnetic units are energized, target DNA molecules are brought into contact with all DNA probes. The target DNA molecules, therefore, undergo hybridization reaction with the probe molecules on the affinity binding regions under the pre-selected hybridization conditions. Alternatively, hybridization can be effected with selected probes by energizing selected electromagnetic units.

Any probes that hybridize to the target DNA molecules can be detected by fluorescence, luminescence or radioactivity depending on the label used on the target molecules. This way a given DNA target can be rapidly screened against a plurality of DNA probes and the results rapidly and automatically quantitated. If the magnetic microbeads interfere with detection, they can be separated from target DNA molecules, for example, by irradiation with 250 nm–750 nm light in the case of a photocleavable linker. The light cleaves the photocleavable linker to disconnect DNA and magnetic beads. The free magnetic beads can then be removed from reaction regions on the chip by additional magnetic forces or washing. Afterwards, the chip can be subjected to "melting" conditions to remove the hybridized target DNA and be reused for a second and for subsequent target DNAs.

The inventors believe the above-described examples show preferred approaches for utilizing this invention.

However, the described parameters such as dimensions, materials, geometries, methods, protocols, temperatures, concentrations and time should not be considered to be the limits of this invention. In addition to the equivalents of the claimed elements, obvious substitutions now or later known to one with ordinary skill in the art are defined to be within the scope of the defined elements. The claims are thus to be understood to include what is specifically illustrated and described above, and what can be obviously substituted. The illustrated embodiment has been set forth only for the purposes of example and that should not be taken as limiting the invention. Therefore, it is to be understood that, within the scope of the appended claims, the invention may be practiced other than as specifically described herein.

We claim:

1. A method for directing reactions between ligand molecules and target molecules, comprising the steps of:

providing a unit having a plurality of individually addressable micro-electromagneticcores;

forming a functional layer for immobilizing ligand molecules above said cores;

providing modified ligand molecules capable of being positioned by magnetic fields;

disposing a solution containing said modified ligand molecules on said functional layer;

creating a pattern of immobilized ligand molecules by selectively energizing said cores to form magnetic fields which position said modified ligand molecules at predetermined locations where said ligand molecules become immobilized on said functional layer;

providing modified target molecules able to be positioned by magnetic fields;

disposing a solution containing said modified target molecules on said pattern of immobilized ligand molecules; and selectively energizing said cores to form magnetic fields which position said modified target molecules in juxtaposition to predetermined immobilized ligand molecules thereby directing a reaction between said target molecules and said ligand molecules.

2. The method of claim 1, further comprising a step of detecting said reaction between said target molecules and said ligand molecules.

3. The method of claim 2, wherein the step of detecting said reaction comprises optical detection.

4. The method of claim 1, wherein said functional layer is selected from the group consisting of a hydrophilic molecular monolayer, a hydrophilic molecular monolayer with functional groups, a hydrophobic molecular monolayer, a hydrophobic molecular monolayer with functional groups, a hydrophilic membrane, a hydrophilic membrane with functional groups, a hydrophobic membrane, a hydrophobic membrane with functional groups, a hydrophilic gel, a hydrophilic gel with functional groups, a hydrophobic gel, a hydrophobic gel with functional groups, a porous material, a porous material with functional groups, a non-porous material and a non-porous material with functional groups.

5. The method of claim 4, wherein said functional groups are selected from the group consisting of aldehydes, carbodiimides, succinimydyl esters, antibodies, receptors, and lectins.

6. The method of claim 1, wherein said modified ligand molecules are ligand molecules linked to magnetic material.

7. The method of claim 6, wherein said ligand molecules are linked to magnetic material by a cleavable linker.

8. The method of claim 7, wherein said cleavable linker is cleavable by light, heat, enzymatic activity or chemical reaction.

9. The method of claim 6, wherein said ligand molecules are linked to magnetic material by a covalent bond.

10. The method of claim 6, wherein said ligand molecules are linked to magnetic material by biological affinity to a molecule coupled to said magnetic material.

11. The method of claim 10, wherein said biological affinity is selected from the group consisting of antibody-antigen affinity, lectin-hapten affinity and receptor-ligand affinity.

12. The method of claim 1, wherein said modified target molecules are target molecules linked to magnetic material.

13. The method of claim 12, wherein said target molecules are linked to magnetic material by a cleavable linker.

14. The method of claim 13, wherein said cleavable linker is cleavable by light, heat, enzymatic activity or chemical reaction.

15. The method of claim 12, wherein said target molecule is linked to magnetic material by a covalent bond.

16. The method of claim 12, wherein said target molecule is linked to magnetic material by biological affinity to a molecule coupled to said magnetic material.

17. The method of claim 16, wherein said biological affinity is selected from the group consisting of antibody-antigen affinity, lectin-hapten affinity and receptor-ligand affinity.

18. The method of claim 1, further comprising the steps of cleaving said modified ligand molecules from a magnetic material or said modified target molecules from a magnetic material or both after the step of selectively energizing magnetic cores, wherein the cleaved modified ligands or cleaved modified target molecules are not substantially positionable by magnetic fields.

19. The method of claim 18, wherein said magnetic material is removed by a magnetic field.

20. The method of claim 18, wherein said magnetic material is removed by a fluid wash.

21. The method of claim 1, wherein said modified ligand molecules are modified by mixing a solution of said ligand molecules with magnetic material, and freezing droplets of ligand molecules mixed with magnetic material to form small solid magnetic particles.

22. The method of claim 21, further comprising the step of using magnetic dispensers to position the small solid magnetic particles on at least one unit.

23. The method of claim 1, wherein said modified ligand and said modified target molecules comprise biological molecules, chemical reagents or pharmaceutical molecules.

24. The method of claim 1, wherein said modified ligand and said modified target molecules comprise nucleic acid molecules.

25. The method of claim 1, wherein one or both of said modified ligand and said modified target molecules comprise antibodies and antigens.

* * * * *